(12) United States Patent
Opfermann et al.

(10) Patent No.: US 11,337,726 B2
(45) Date of Patent: May 24, 2022

(54) APPARATUS FOR ACCESSING THE PERICARDIAL SPACE

(71) Applicant: CHILDREN'S NATIONAL MEDICAL CENTER, Washington, DC (US)

(72) Inventors: Justin Opfermann, Washington, DC (US); Charles Berul, Washington, DC (US); Bradley Clark, Bronx, NY (US); Axel Krieger, College Park, MD (US); Rohan Kumthekar, Washington, DC (US); Paige Mass, Washington, DC (US); Austeja Staneviciute, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 174 days.

(21) Appl. No.: 16/626,761

(22) PCT Filed: Jul. 2, 2018

(86) PCT No.: PCT/US2018/040620
§ 371 (c)(1),
(2) Date: Dec. 26, 2019

(87) PCT Pub. No.: WO2019/006460
PCT Pub. Date: Jan. 3, 2019

(65) Prior Publication Data
US 2020/0121360 A1 Apr. 23, 2020

Related U.S. Application Data

(60) Provisional application No. 62/527,568, filed on Jun. 30, 2017.

(51) Int. Cl.
*A61B 17/34* (2006.01)
*A61B 90/00* (2016.01)
(Continued)

(52) U.S. Cl.
CPC ...... *A61B 17/3423* (2013.01); *A61B 17/3468* (2013.01); *A61B 2017/00243* (2013.01);
(Continued)

(58) Field of Classification Search
CPC .. A61B 1/01; A61B 1/32; A61B 17/34; A61B 17/3421; A61B 17/3423;
(Continued)

(56) References Cited

U.S. PATENT DOCUMENTS

2002/0042605 A1 4/2002 Castaneda et al.
2003/0060685 A1 3/2003 Houser et al.
(Continued)

FOREIGN PATENT DOCUMENTS

CA 2002851 5/1990

OTHER PUBLICATIONS

International Search Report and Written Opinion dated Sep. 7, 2018 in PCT/US2018/040620 filed Jul. 2, 2018 (9 pages).
(Continued)

*Primary Examiner* — George J Ulsh
(74) *Attorney, Agent, or Firm* — Oblon, McClelland, Maier & Neustadt, L.L.P.

(57) ABSTRACT

The present disclosure relates to devices used to access the pericardial space of the heart. In particular, the present disclosure describes an apparatus to enable an operator to access the pericardial space of the heart, and deliver cardiac therapies to the pericardial space, under direct visualization through a single, small incision.

20 Claims, 35 Drawing Sheets

(51) Int. Cl.
   *A61B 17/00* (2006.01)
   *A61N 1/362* (2006.01)
(52) U.S. Cl.
   CPC ............... *A61B 2017/00526* (2013.01); *A61B 2017/00867* (2013.01); *A61B 2017/3425* (2013.01); *A61B 2017/3447* (2013.01); *A61B 2017/3486* (2013.01); *A61B 2017/3488* (2013.01); *A61B 2090/363* (2016.02); *A61N 1/362* (2013.01)
(58) Field of Classification Search
   CPC ............ A61B 17/3462; A61B 17/3468; A61B 2017/00526; A61B 2017/00867; A61B 2017/3425; A61B 2017/3427; A61B 2017/3429; A61B 2017/3445; A61B 2017/3447; A61B 2017/3466; A61B 2017/3484; A61B 2017/3486; A61B 2017/3488; A61B 2090/061
   See application file for complete search history.

(56) References Cited

U.S. PATENT DOCUMENTS

| | | | |
|---|---|---|---|
| 2004/0236347 A1 | 11/2004 | Karasawa | |
| 2005/0043592 A1 | 2/2005 | Boyd et al. | |
| 2006/0129165 A1 | 6/2006 | Edoga et al. | |
| 2007/0213675 A1* | 9/2007 | Albrecht | A61B 17/3421 604/264 |
| 2009/0105655 A1 | 4/2009 | DeSantis et al. | |
| 2009/0326462 A1 | 12/2009 | Wingardner, III et al. | |
| 2010/0280327 A1* | 11/2010 | Nobis | A61B 17/3423 600/210 |
| 2010/0286484 A1* | 11/2010 | Stellon | A61B 17/3462 600/208 |
| 2011/0071347 A1 | 3/2011 | Rogers et al. | |
| 2011/0082343 A1 | 4/2011 | Okoniewski | |
| 2012/0130191 A1 | 5/2012 | Pribanic | |
| 2012/0157781 A1* | 6/2012 | Kleyman | A61B 17/0218 600/208 |
| 2012/0296358 A1 | 11/2012 | Nguyen et al. | |
| 2014/0018632 A1* | 1/2014 | Kleyman | A61B 17/0218 600/208 |
| 2014/0018732 A1 | 1/2014 | Bagaoisan et al. | |
| 2014/0121466 A1 | 5/2014 | Okoniewski | |
| 2017/0027553 A1 | 2/2017 | Kleyman | |
| 2017/0112530 A1 | 4/2017 | Fowler et al. | |

OTHER PUBLICATIONS

Extended European Search Report dated Mar. 30, 2021 in European Patent Application No. 18825402.3, citing documents AA-AH therein, 7 pages.

* cited by examiner

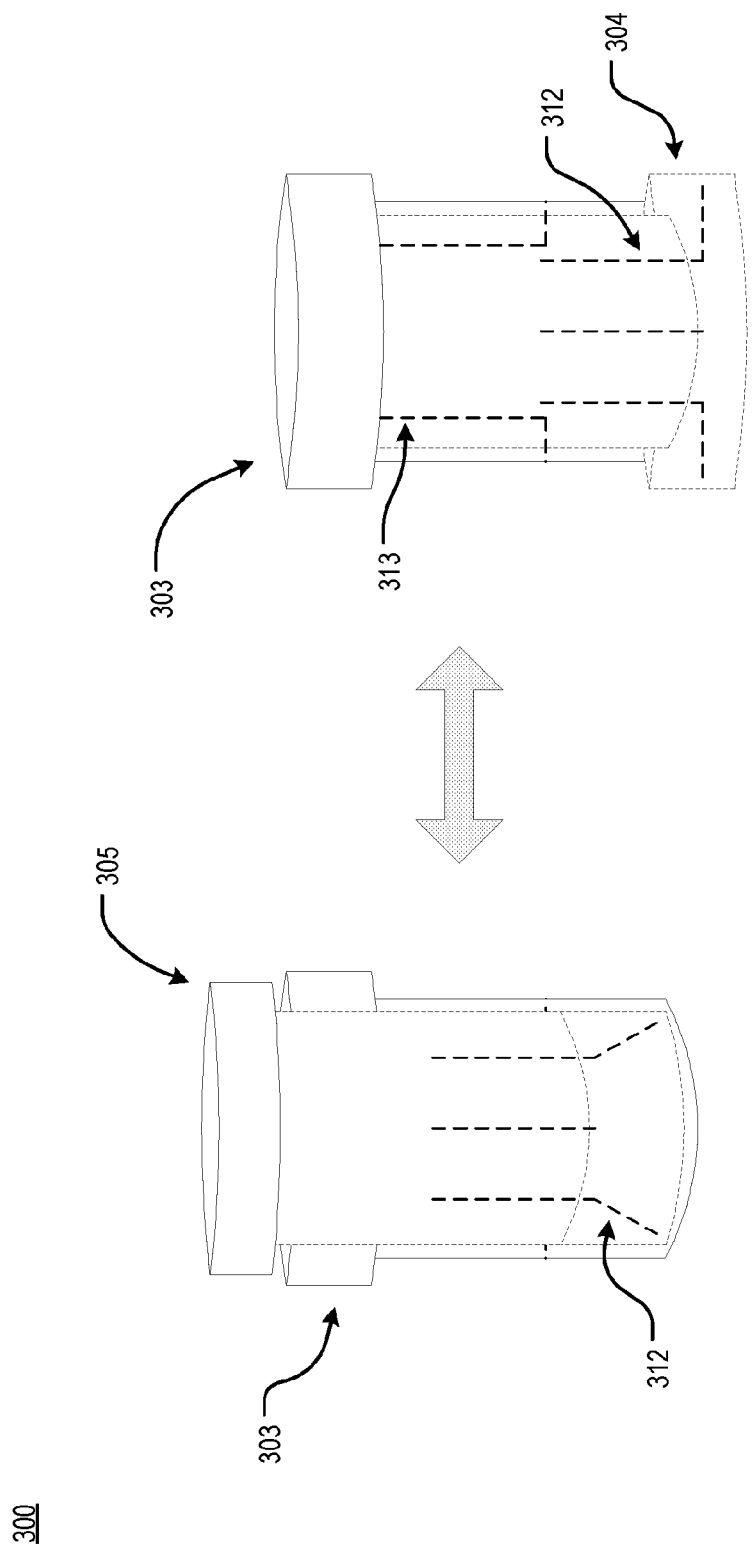

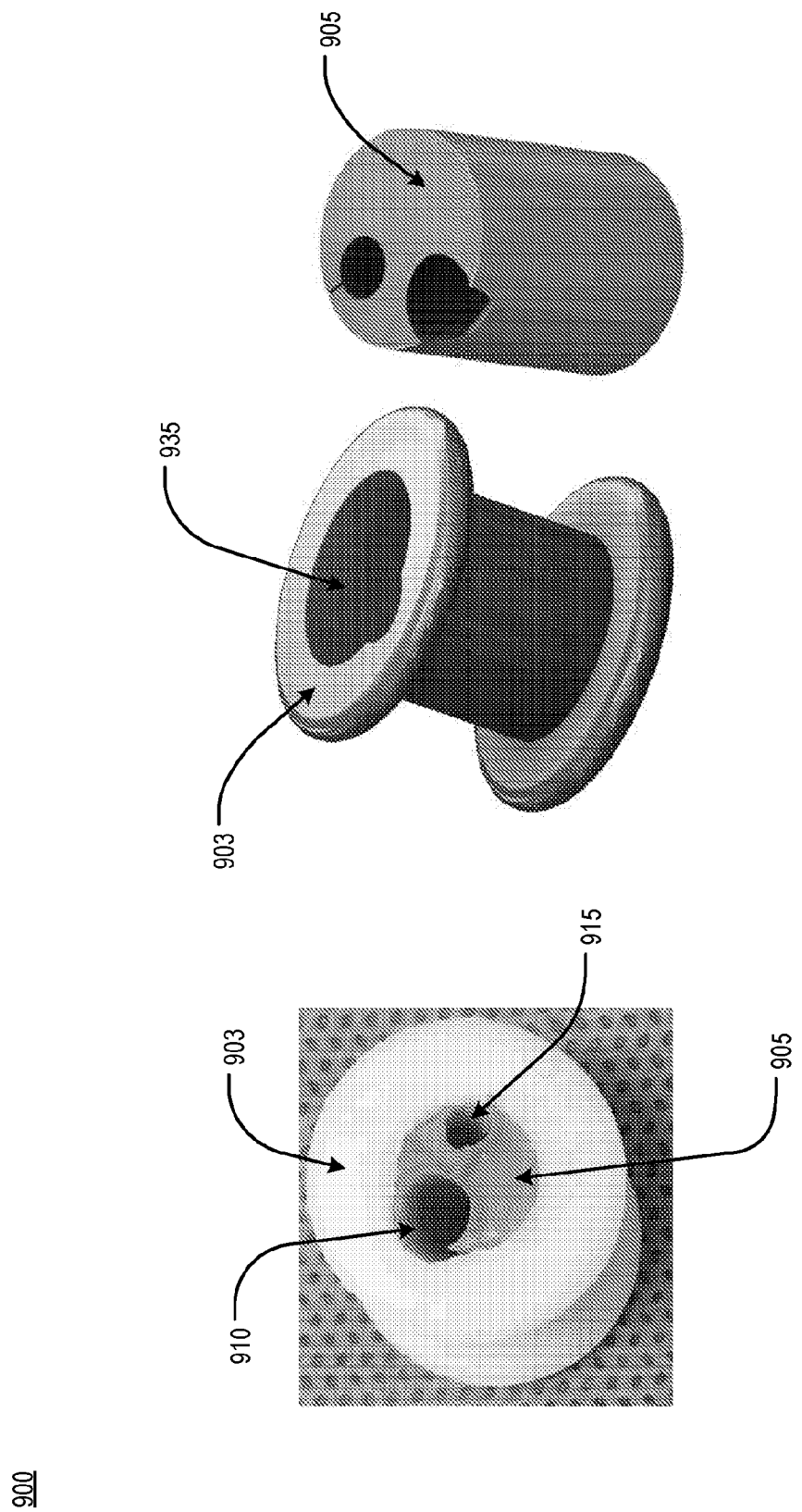

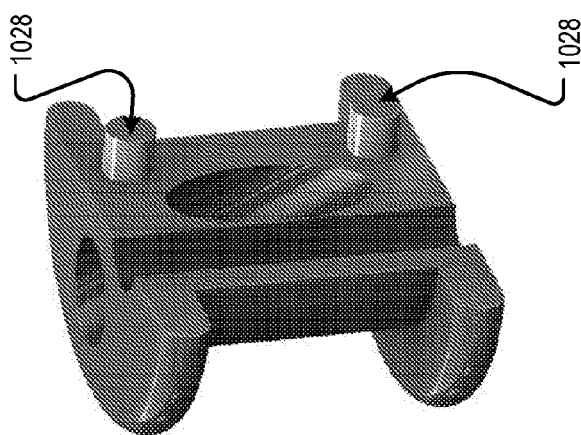
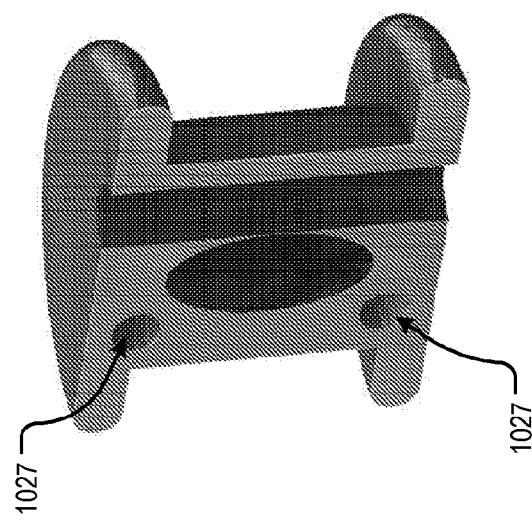
FIG. 10B
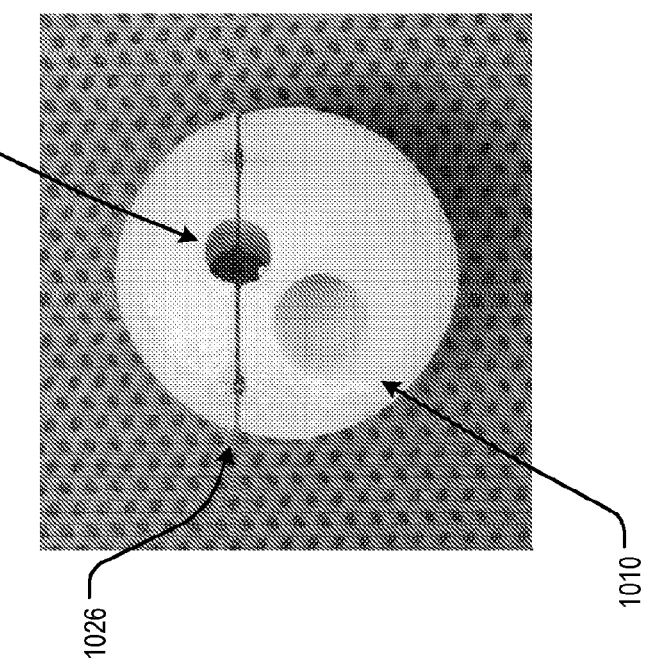
FIG. 10A

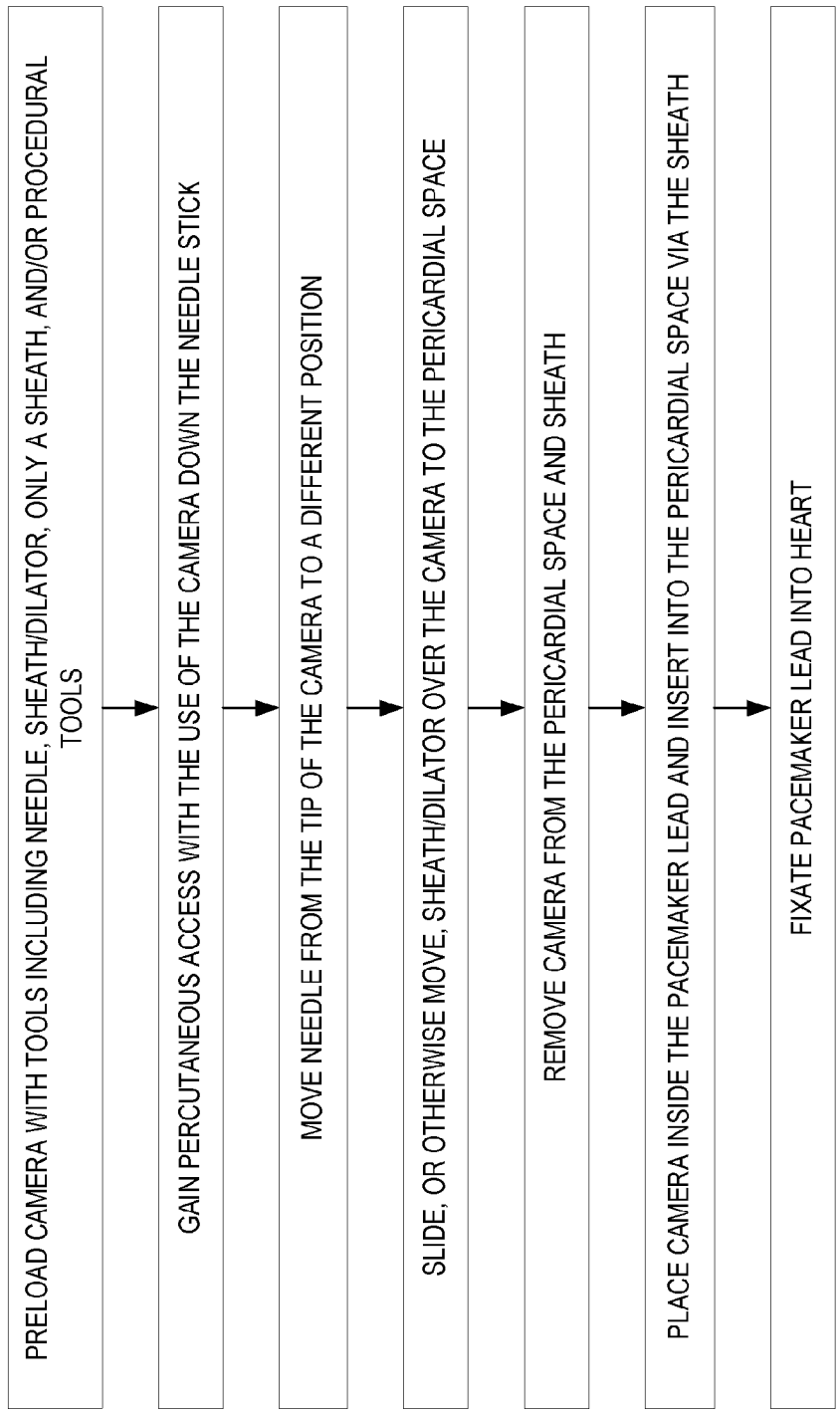

APPARATUS FOR ACCESSING THE PERICARDIAL SPACE

CROSS-REFERENCE TO RELATED APPLICATIONS

The present application claims priority to U.S. Provisional Application No. 62/527,568, filed Jun. 30, 2017 the teachings of which are hereby incorporated by reference in its entirety for all purposes. In addition, U.S. application Ser. No. 14/625,350, filed Feb. 18, 2015, is also hereby incorporated by reference in its entirety for all purposes.

BACKGROUND

Field of the Disclosure

The present disclosure relates to the field of cardiac rhythm therapy, and an apparatus for enabling access to the pericardial space under direct visualization and control for medical device delivery.

Description of the Related Art

Cardiac pacing may be utilized to stimulate the heart. Currently, two distinct approaches to implantation of medical devices for cardiac pacing are performed: (1) transvenous access of the endocardium or (2) direct surgical access to the epicardial surfaces. When it becomes necessary to implant a cardiac pacemaker in small children or patients with congenital heart defects, however, cardiologists and surgeons are presented with a unique set of challenges. These patients are often too small for insertion of pacemaker leads through a transvenous approach and congenital anomalies of the heart or venous system may complicate or prevent transvenous lead placement. Further to small body habitus and limited venous capacitance, other contraindications to transvenous pacing may include intracardiac shunts, venous obstruction, endocarditis, mechanical tricuspid valve, and complex venous anatomy resulting in an inability to access the right heart endocardium. Moreover, patients with congenital heart disease and device-dependent primary electrical diagnoses are likely to require multiple invasive procedures over the course of a lifetime with attendant cumulative risk of venous occlusion, therefrom.

For instance, cardiac resynchronization therapy for left ventricular failure and dyssynchrony may be performed via transvenous approach in adults and older children with structurally normal hearts. However, in smaller patients or those with particular forms of congenital heart disease that result in structurally abnormal hearts, epicardial pacing remains the conventional technique.

Significantly elevating risks to the patient, epicardial lead placement requires gaining direct surgical access to the heart via a significantly invasive approach including sternotomy and thoracotomy. Post-operative recovery, therefore, typically entails multiple days in an intensive care unit with commensurate costs and risks. Patients undergoing sternotomy may also be at increased risk of intrathoracic adhesions and heightened subsequent operative risk of reentry injury, should the need for reoperation or exploration arise. In such cases, fibrotic tissue must be fully dissected in order to reach viable cardiac tissue for acceptable pacing thresholds, thus complicating reoperation and hindering successful outcomes.

Most of the approved technologies used to implant devices for managing cardiac rhythm disease, are delivered via transvenous approach and rely on patient vasculature for navigation under intermediate exposure to fluoroscopy. For pediatric, single ventricle, and abnormal vasculature patients, however, a transvenous approach is not feasible due to anatomical restrictions in navigation. This patient population, typically subjected to either thoracotomy or equivalent procedure to expose the heart and allow direct access to the pericardium, may benefit from a minimally invasive approach to implantation of epicardial devices as described in the present disclosure.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to an apparatus for transcutaneous delivery of a medical therapy, comprising a shell, a core, concentrically disposed within the shell, including one or more working channels, the one or more working channels including a first working channel and a second working channel, a proximal flange disposed at a proximal end of the shell, and a distal flange disposed at a distal end of the shell, wherein the first working channel and the second working channel are offset by a triangulation angle, the triangulation angle describing a relative arrangement of a longitudinal axis of the first working channel and a longitudinal axis of the second working channel, and wherein an aperture of the first working channel is larger than an aperture of the second working channel.

According to an embodiment, the present disclosure further relates to a method of manufacturing an apparatus for transcutaneous delivery of a medical therapy, comprising forming, via a subtractive manufacturing modality, a shell having a proximal flange disposed at a proximal end of the shell and a distal flange disposed at a distal end of the shell, forming, via the subtractive manufacturing modality, a core including one or more working channels, the one or more working channels including a first working channel and a second working channel, and positioning the core concentrically within the shell, wherein the first working channel and the second working channel are offset by a triangulation angle, the triangulation angle describing a relative arrangement of a longitudinal axis of the first working channel and a longitudinal axes of the second working channel, and wherein an aperture of the first working channel is larger than an aperture of the second working channel.

According to an embodiment, the present disclosure further relates to a method of manufacturing an apparatus for transcutaneous delivery of a medical therapy, comprising forming, via an additive manufacturing modality, a shell having a proximal flange disposed at a proximal end of the shell and a distal flange disposed at a distal end of the shell, and forming, via the additive manufacturing modality, a core disposed concentrically within the shell and including one or more working channels, the one or more working channels including a first working channel and a second working channel, wherein the first working channel and the second working channel are offset by a triangulation angle, the triangulation angle describing a relative arrangement of a longitudinal axis of the first working channel and a longitudinal axes of the second working channel, and wherein an aperture of the first working channel is larger than an aperture of the second working channel.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3C is a flowchart of an anchoring process of an apparatus for accessing a pericardial space, according to an exemplary embodiment of the present disclosure;

FIG. 9A is an illustration featuring one or more working channels of an apparatus for accessing a pericardial space, according to an exemplary embodiment of the present disclosure;

FIG. 9B is an illustration featuring one or more working channels of an apparatus for accessing a pericardial space, according to an exemplary embodiment of the present disclosure;

FIG. 10A is an illustration featuring a locking feature of an apparatus for accessing a pericardial space, according to an exemplary embodiment of the present disclosure;

FIG. 10B is an illustration featuring a locking feature of an apparatus for accessing a pericardial space, according to an exemplary embodiment of the present disclosure;

FIG. 32 is a flowchart describing a preloaded needle for pericardial access, according to an exemplary embodiment of the present disclosure.

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

According to an embodiment, the present disclosure relates to an apparatus for use in a surgical field. While preferred embodiments are disclosed, herein, it can be understood that the presented embodiments are merely exemplary and may be embodied in other forms. Therefore, the specific design, features, and functionality of the disclosed are not to be interpreted as limiting, but to serve a basis for the claims, and to educate one skilled in the art as to the functionality of the embodiments with respect to performing a task in any surgical field. Further, it can be appreciated that the following drawings are described in order to draw attention to specific features of the present disclosure and are not intended to, in each instance, be exhaustive descriptions of functionality. To this end, and for the purposes of teaching, the preferred embodiments, in a non-limiting manner, are directed to device anchoring, triangulation of tools in the surgical field, and methods to accommodate therapies of various sizes.

Figure 1B:
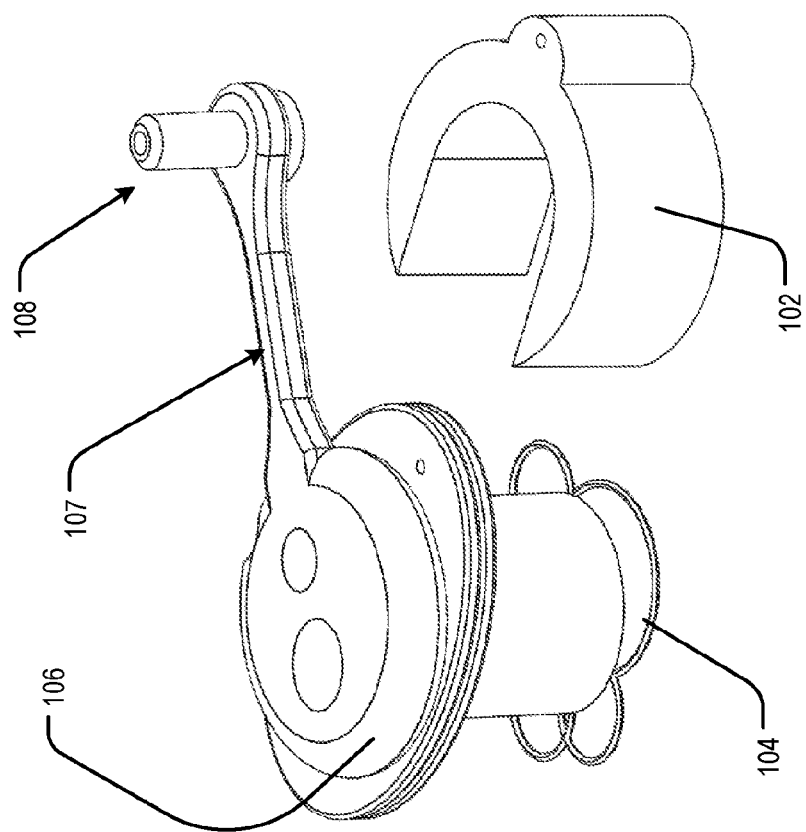
FIG. 1B is a schematic featuring a distal flange of an apparatus for accessing a pericardial space, according to an exemplary embodiment of the present disclosure.
Figure 1A:
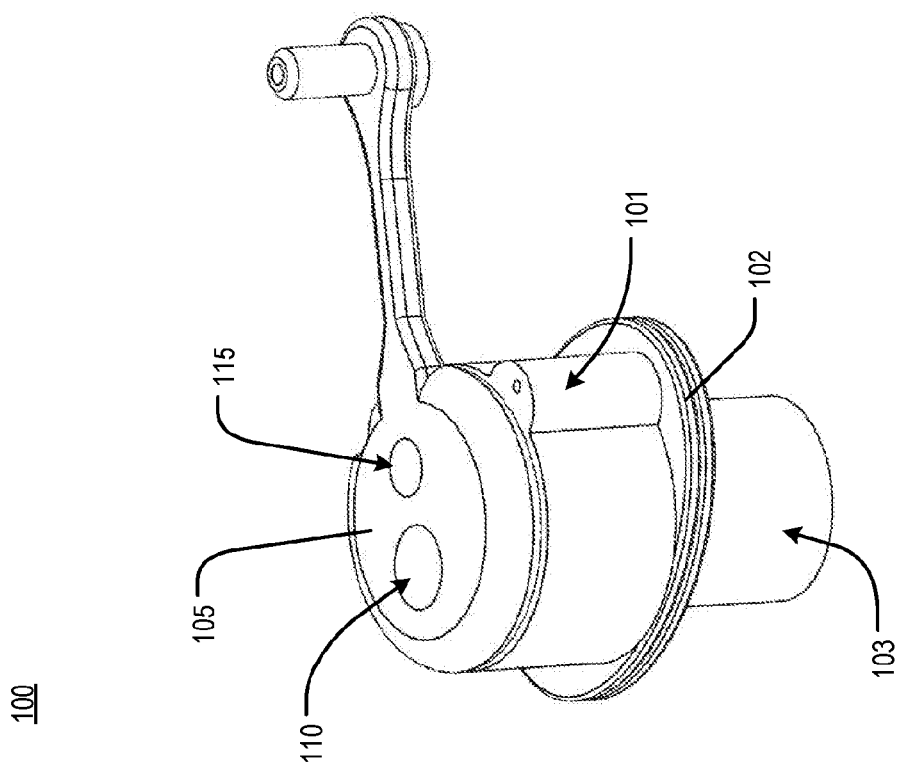
FIG. 1A is a schematic of an apparatus for accessing a pericardial space, according to an exemplary embodiment of the present disclosure.

According to an embodiment, the present disclosure relates to an apparatus for accessing a pericardial space, referred to herein as an access apparatus. With reference to FIG. 1A and FIG. 1B, an access apparatus 100 may comprise a shell 103, a spacer 101, a core 105, a first working channel 110 and a second working channel 115 of one or more working channels, a proximal flange 102, and a distal flange 104. In an embodiment, the distal flange 103 may be disposed at a distal end of the core 105 or at the distal end of the shell 103. With reference to FIG. 1B, a core flange 106 may be disposed between the core 105 and the proximal flange 102. Further, a plug 108 may be attached to the core 105 via a tether 107. In an embodiment, the plug 108 may be substantially cylindrical and may have an aperture 132. The aperture 132 of the plug 108 may be of a diameter configured to decrease an aperture of one of the one or more working channels in order to, for example, allow passage of and retention of a surgical instrument of reduced diameter. In another embodiment, one or more plugs 108 may be attached to the core 105 via a corresponding one or more tethers 107. Each of the one or more plugs 108 may be configured to modify an aperture of one of the one or more working channels, in a manner similar to that described above for a single plug 108.

According to an embodiment, the plug 108 tethered to the core 105 may be a valve to control movement of equipment. In another embodiment, the aperture of the plug 108 tethered to the core 105 may be a valve in order to accommodate a variety of differently-sized tools.

Access Apparatus Anchoring

According to an embodiment, to ensure insufflation of the patient and to allow unimpeded access to the surgical field, the access apparatus 100 may anchored transcutaneously to the chest wall of the patient.

In an embodiment, the access apparatus 100 may be in one of two states: an insertion state or a locked state. In the insertion state, the distal flange 104 may be folded into the shell 103 of the access apparatus 100 and held in position by the spacer 102, which maintains a distance between the proximal flange 102 and a surface of the core 105. Following insertion, and in order to secure the access apparatus 100 transcutaneously across the integument of a patient, the spacer 102 may be removed and the core 105 may be pushed through the shell 103. Upon sufficient travel of the core 105 through the shell 103, the distal flange 104 may be forced out of the shell 103 and into a relaxed form, as shown in FIG. 1B, within the body of the patient. In an embodiment, the distal flange 104 may act to secure the access apparatus 100 transcutaneously, with the distal flange 104 being inside the patient, thereby preventing movement of the access apparatus 100 by forces that may be applied from inside of or outside the patient. Concurrently, and in an embodiment, the proximal flange 102 may secure the access apparatus 100 to an external surface of the skin of the patient, thereby similarly preventing movement of the access apparatus 100 by forces that may be applied from inside of or outside the patient.

According to an embodiment, the access apparatus 100 may be fabricated from a variety of materials suitable for medical devices including but not limited to polyvinylidene fluoride, polyethylene, polypropylene, polydimethylsiloxane, parylene, polyamide, polytetrafluoroethylene, poly(methyl methacrylate), polyimide, polyurethane, or a combination thereof.

In another embodiment, and in order to secure the access apparatus 100 transcutaneously, the distal flange 104 may be a mutable flange, deployable under pre-determined situations. The distal flange 104 may be fabricated from a shape-memory alloy selected from a group including but not limited to copper-aluminum-nickel and nickel-titanium, or alloys of zinc, copper, gold, and iron. To this end, the distal flange 104 may be deformed in an insertion state but relaxed to a pre-deformed state upon physiologic heating in the locked state. In an example, the deformed state of the distal flange 104 may be a straightened state, wherein, upon being pushed transcutaneously, the distal flange 104 may return to a relaxed state, or bent state, thus securing the access apparatus 100 to the chest wall of the patient.

Alternatively, the deformable, or mutable, nature of the distal flange 104 may be achieved by fabrication via materials that may be modified through application of external energy, including ultrasound, magnetism, or electricity, via mechanical action including but not limited to springs, or via naturally-deformable materials including but not limited to rubber, polysiloxane, and polydimethylsiloxane.

Figure 2B:
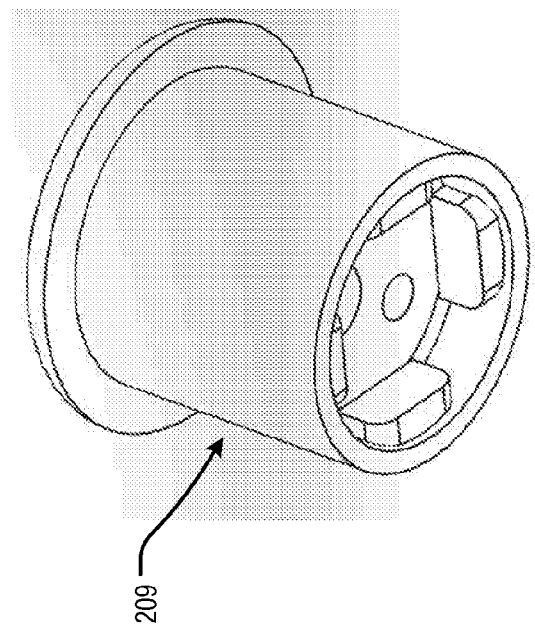
FIG. 2B is a schematic featuring a distal flange of an apparatus for accessing a pericardial space, according to an exemplary embodiment of the present disclosure.
Figure 2A:
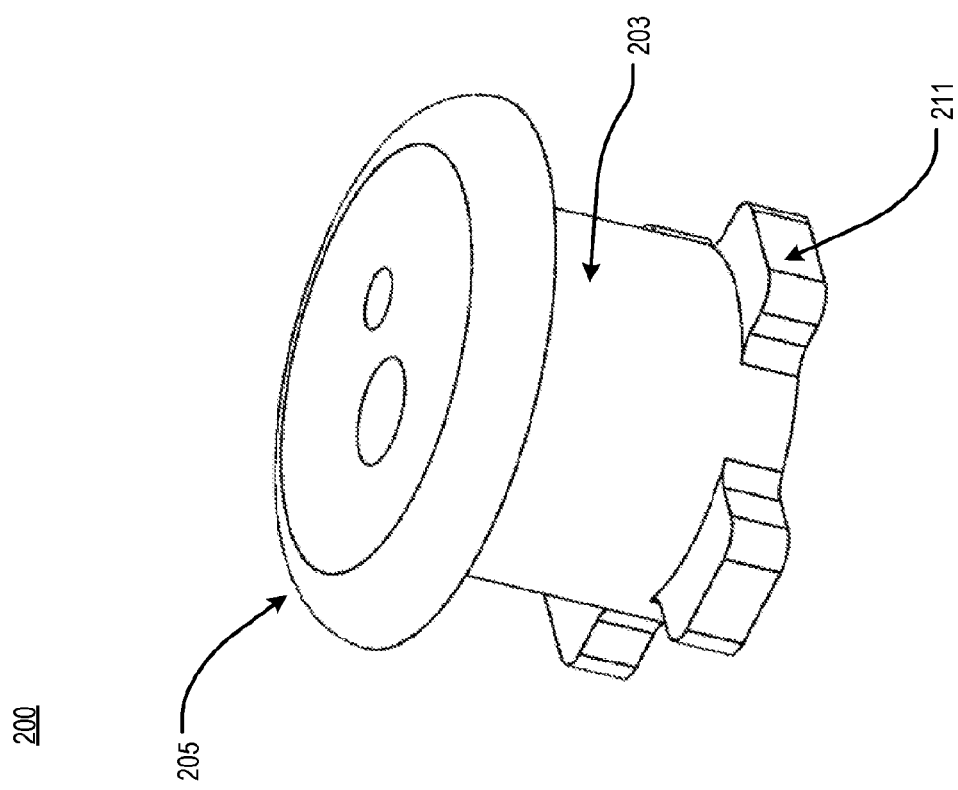
FIG. 2A is a schematic featuring a distal flange of an apparatus for accessing a pericardial space, according to an exemplary embodiment of the present disclosure.

According to an embodiment, the access apparatus of the present disclosure, and the distal flange, therein, may be fabricated from the same material. Further, the distal flange may be fabricated integrally within the shell of the access apparatus, as shown in FIG. 2A. Accordingly, FIG. 2A is a schematic featuring a distal flange of an apparatus for accessing a pericardial space. According to an exemplary embodiment of the present disclosure, an access apparatus 200 may comprise a core 205, a shell 203, and one or more distal flanges integrally disposed at a distal end of the shell 203. In an embodiment, the one or more distal flanges are one or more flaps 211. During insertion, as shown in FIG. 2B the one or more flaps 211 may be deformed within a sleeve 209 in order to enable rapid and easy insertion within the patient. Upon insertion, however, the sleeve 209 may be removed from the access apparatus 200. As a result, the deformable, or mutable, one or more flaps 211 may return to an original, pre-deformed position, thus securing the distal portion of the access apparatus 200 transcutaenously.

According to an embodiment, the one or more flaps 211 may be mutable, deployable under pre-determined situations. To this end, the one or more flaps 211 may be fabricated from a shape-memory alloy selected from a group including but not limited to copper-aluminum-nickel and nickel-titanium, or alloys of zinc, copper, gold, and iron. Further, the one or more flaps 211 may be deformed in a straightened state when in an insertion state but return to a pre-deformed, bent state upon being in a locked state.

Alternatively, the deformable nature of the one or more flaps 211 may be achieved by fabrication via materials that may be modified through application of external energy, including ultrasound, magnetism, or electricity, via mechanical action including but not limited to springs, or via naturally-deformable materials including but not limited to rubber, polysiloxane, and polydimethylsiloxane.

Figure 3B:
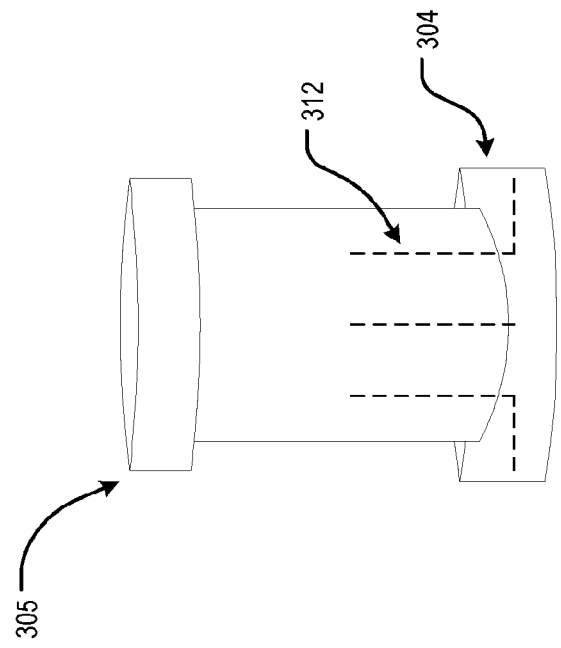
FIG. 3B is a schematic featuring a shapeable material of a core of an apparatus for accessing a pericardial space, according to an exemplary embodiment of the present disclosure.
Figure 3A:
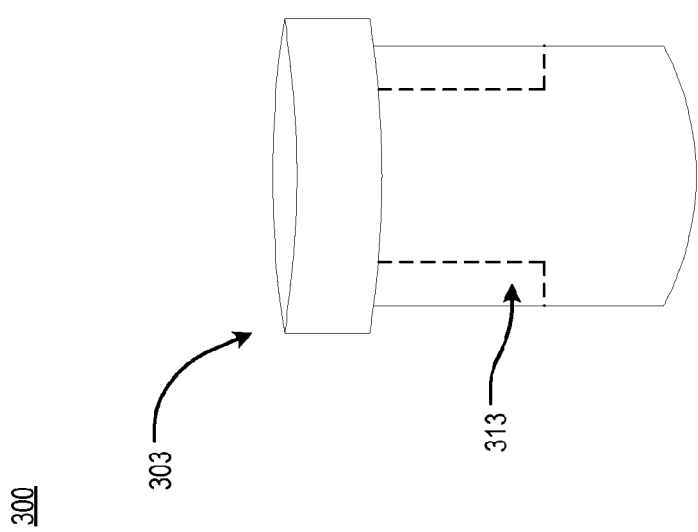
FIG. 3A is a schematic of a shell of an apparatus for accessing a pericardial space, according to an exemplary embodiment of the present disclosure.

Moreover, in an embodiment, the one or more flaps 211 may be fabricated via a combination of the above-described materials. To this end, and as shown in the cross-sectional schematics of FIG. 3A, FIG. 3B, and FIG. 3C, an access apparatus 300 may comprise a sleeve 309 having one or more orienting slots 313 and a core 305 having one or more tines 312 embedded therein. In an embodiment, the sleeve 309 may be fabricated from a variety of materials suitable for medical devices including but not limited to polyvinylidene fluoride, polyethylene, polypropylene, polydimethylsiloxane, parylene, polyamide, polytetrafluoroethylene, poly(methyl methacrylate), polyimide, polyurethane, or a combination thereof. In another embodiment, the core 305 may be fabricated from a combination of deformable materials including but not limited to shape-memory alloys, materials that may be modified via application of external energy, including ultrasound, magnetism, or electricity, materials that may be modified via mechanical action including but not limited to springs, or naturally-deformable materials including but not limited to rubber, polysiloxane, and polydimethylsiloxane. In an example, the core 305 may be fabricated from polysiloxane and the one or more tines 312 may be shape-memory alloys. The one or more tines 312 may be disposed within the polysiloxane core 305 and may extend from a central portion of the core 305 to a distal portion of the core 305, ending in a distal flange 304. As shown in FIG. 3B, the core 305 may be in a locked state, wherein the shape-memory alloy of the one or more tines 312 are in a pre-deformed, bent shape. Alternatively, the core 305 may be in an insertion state, wherein the one or more tines 312 are in a deformed, straightened state. Specifically, as shown in FIG. 3C, the core 305 may be fitted within the sleeve 309 such that one or more orienting posts (not shown) of the core 305 are secured within the one or more orienting slots 313 and the one or more tines 312 are deformed in order to fit within the sleeve 309. Following insertion of the access apparatus 300 within the patient, the sleeve 309 may be removed and the one or more tine 312 may return to a pre-deformed, bent shape, as shown in FIG. 3B. In returning to the pre-deformed shape, the one or more tines 312 may form the distal flange 304, securing the access apparatus 300 transcutaenously. The process of shifting from the insertion state to the locked state may be reversible.

Figure 4:
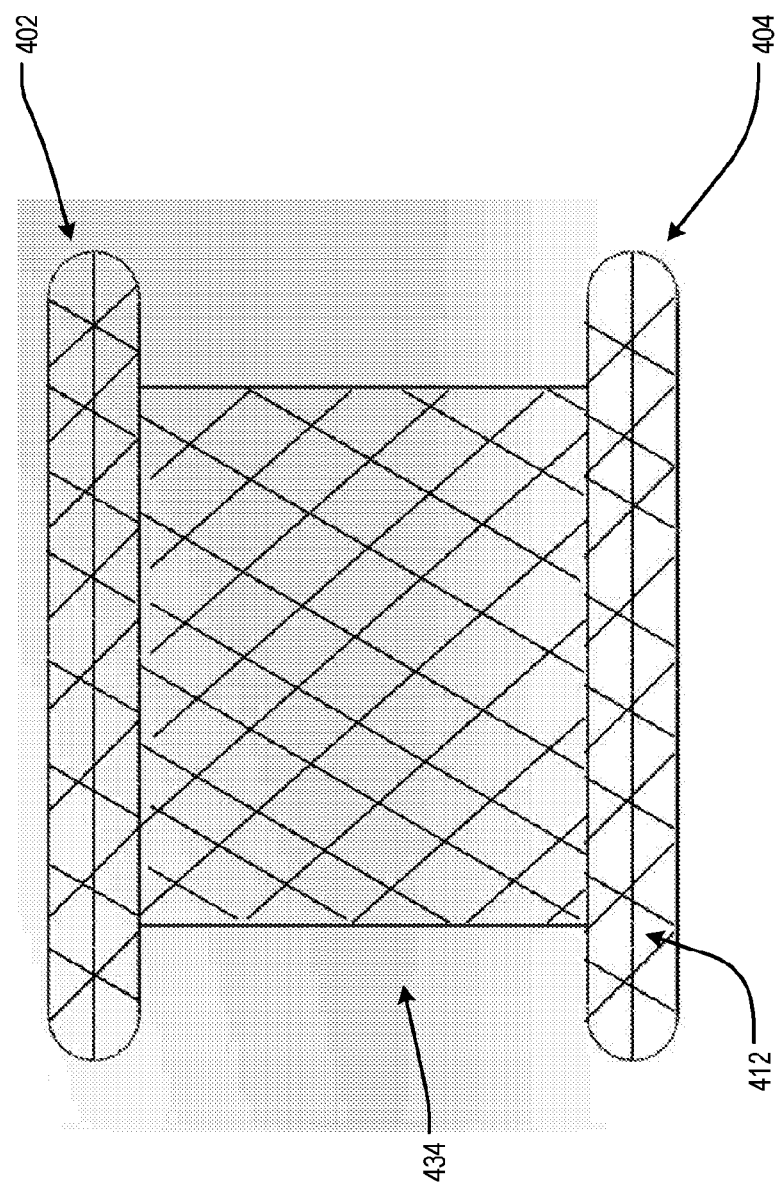
FIG. 4 is a schematic featuring a shapeable material of an apparatus for accessing a pericardial space, according to an exemplary embodiment of the present disclosure.

According to an embodiment, the above-combination of soft materials and rigid materials within the core 305 ensure insufflation when the access apparatus 300 is positioned transcutaneously. To this end, as shown in FIG. 4, the access apparatus 400 may be fabricated from a combination of soft materials and rigid materials. In an embodiment, the access apparatus 400 may be comprised of a network of tines 434 embedded within a polymeric material. In an example, the network of tines 434 may be comprised of a network of shape-memory alloys selected from the group including but not limited to copper-aluminum-nickel and nickel-titanium, or alloys of zinc, copper, gold, and iron, while the polymeric material may be fabricated from a material including but not limited to polysiloxane and polydimethylsiloxane. The orientation and arrangement of the one or more tines 412 of the network of tines 434 may be determined according to a desired shape of the access apparatus 400 in an insertion state and in a locked state. Through implementation of the above-described combination approach, the access apparatus 400 is able to exist in the insertion state and the locked state, wherein the insertion state comprises a deformed state and the locked state comprises a pre-deformed state. Upon insertion, the access apparatus 400 may return to the pre-deformed state, thus securing the access apparatus 400 transcutaneously via a mutable, distal flange 404 and a proximal flange 402.

Figure 5B:
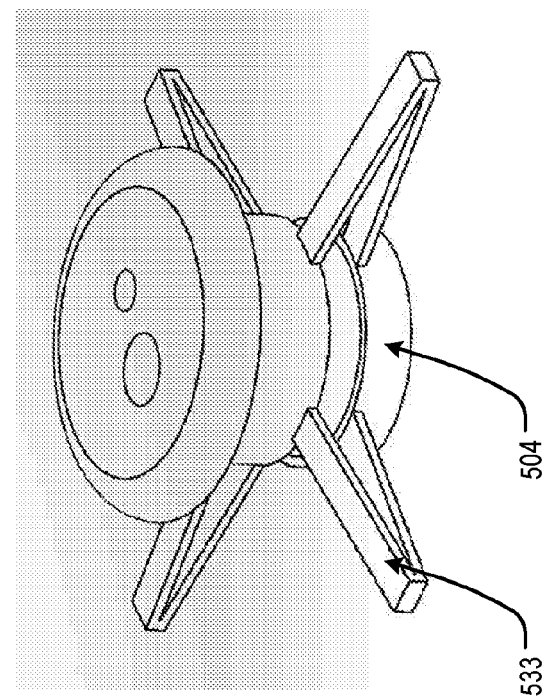
FIG. 5B is a schematic featuring a shapeable material of an apparatus for accessing a pericardial space, according to an exemplary embodiment of the present disclosure.
Figure 5A:
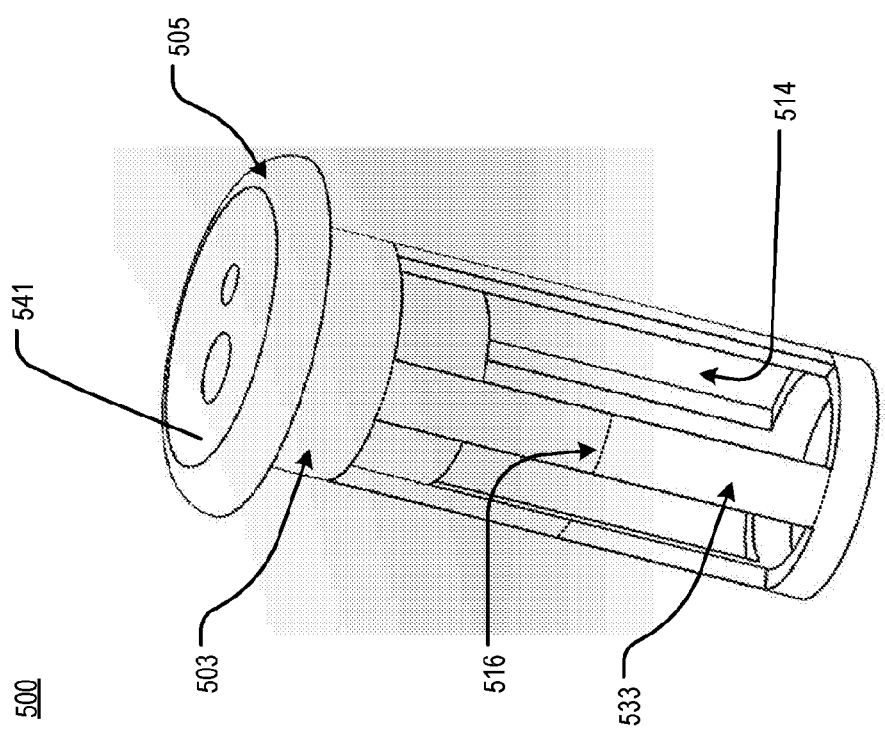
FIG. 5A is a schematic featuring a shapeable material of an apparatus for accessing a pericardial space, according to an exemplary embodiment of the present disclosure.

According to an embodiment of the present disclosure, and in order to secure an access apparatus to the chest wall, the access apparatus may employ a folding geometry. FIG. 5A and FIG. 5B are schematics featuring a folding feature of an apparatus for accessing a pericardial space, in an insertion state and a locked state, respectively. Specifically, FIG. 5A is an access apparatus 500 comprising a core 505 and a shell 503. The shell 503, extending from a proximal portion of the access apparatus 500 to a distal portion of the access apparatus 500, may comprise one or more slits 514 of a pre-determined geometry. The one or more slits 514 of a pre-determined width may extend along a longitudinal axis of the access apparatus 500 for a pre-determined length. One or more struts 533 are positioned between each of the one or more slits 514 and comprise one or more biasing features 516. The spacing, thickness, and depth of each of the above-described features, combined with the geometry of the one or more slits 514, may influence the shape of an access tool. To this end, each of the one or more biasing features 516 may preferentially deform the one or more struts 533 outwardly, as shown in FIG. 3B, upon a pushing force or a pulling force at a proximal end of the access apparatus 500. In the insertion state, the one or more struts 533 may be substantially perpendicular to an extracorporeal surface 541 of the access apparatus 500. Upon insertion, however, the one or more struts 533 deform at the one or more biasing features 516, resulting in the access apparatus 500 being in the locked state and forming a distal flange 504 for securing the access apparatus 500 transcutaneously. In an embodiment, the locked state may be achieved by engaging a screw and thread mechanism that pulls the distal flange 504 toward the proximal end of the access apparatus 500, thus deforming the one or more struts 533.

Figure 6B:
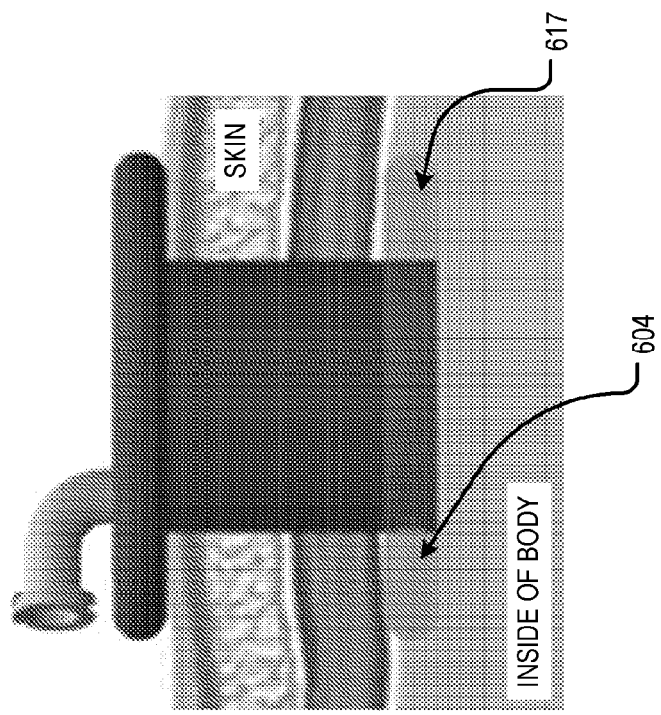
FIG. 6B is an illustration featuring a distal flange of an apparatus for accessing a pericardial space, according to an exemplary embodiment of the present disclosure.
Figure 6A:
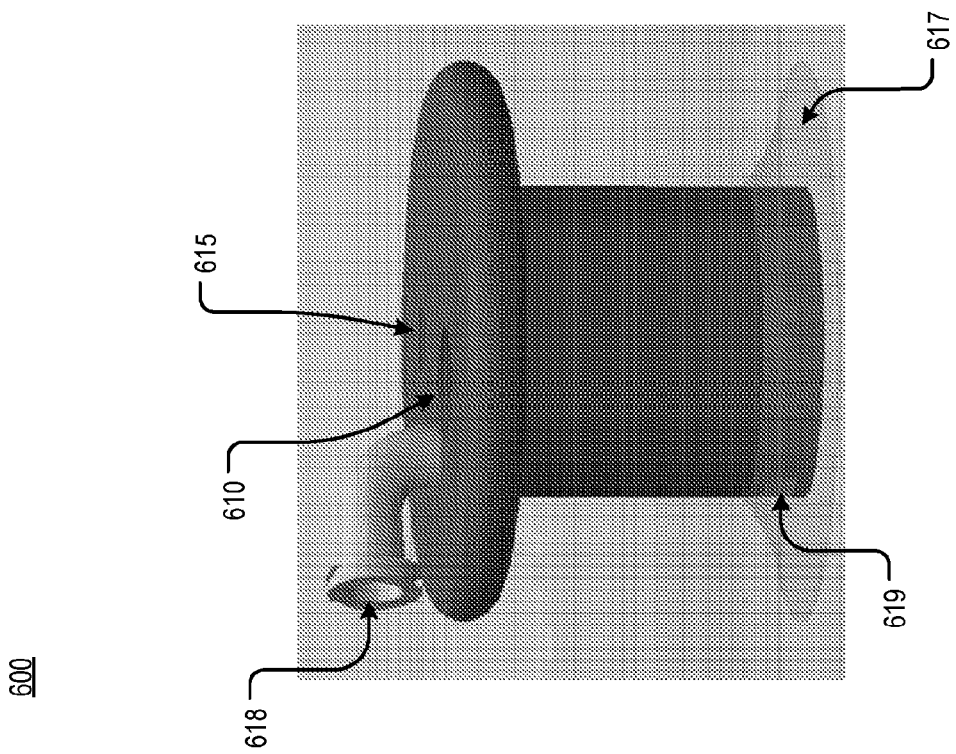
FIG. 6A is an illustration featuring a distal flange of an apparatus for accessing a pericardial space, according to an exemplary embodiment of the present disclosure.

According to another embodiment, and as shown in FIG. 6A and FIG. 6B, a mutable, distal flange 604 of an access apparatus 600 may be an inflatable flange 617 that is selectively or permanently fixed to a distal portion of the access apparatus 600. Adjacent to a first working channel 610 and a second working channel 615, an inlet 618, in fluid communication with an outlet 619, provides a conduit between the extracorporeal space and the inside of the patient. In an embodiment, the inlet 618 may be disposed at a variety of positions within the access apparatus 600 such that a transcutaneous conduit is provided. This conduit may be accessed to provide a fluid to the inflatable flange 617. FIG. 6A is an illustration of the access apparatus 600 in an insertion state, wherein the inflatable flange 617 may be deflated. FIG. 6B, therefore, is an illustration of the access apparatus 600 in a locked state, according to an exemplary embodiment of the present disclosure. Following insertion, a fluid, gas, liquid, or otherwise, may be provided to the inflatable flange 617 via the inlet and outlet of the access apparatus 600. In an embodiment, the inlet 618 may be configured to be compatible with a syringe such that a user may inflate the inflatable flange 617 via sterile fluid. Once in an inflated state, the inflatable flange 617 secures the access apparatus 600 transcutaneously.

Camera Triangulation

According to an embodiment, and in an effort to enhance visualization of the surgical field, the present disclosure describes a plurality of approaches for triangulation.

Figure 7B:
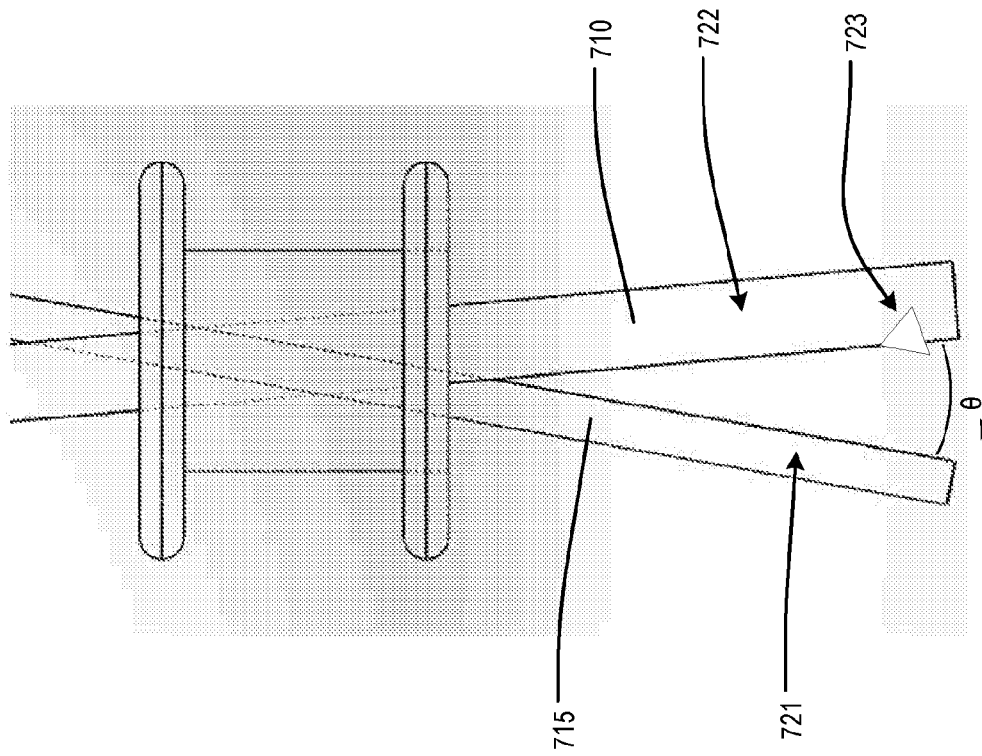
FIG. 7B is a schematic featuring one or more working channels of an apparatus for accessing a pericardial space, according to an exemplary embodiment of the present disclosure.
Figure 7A:
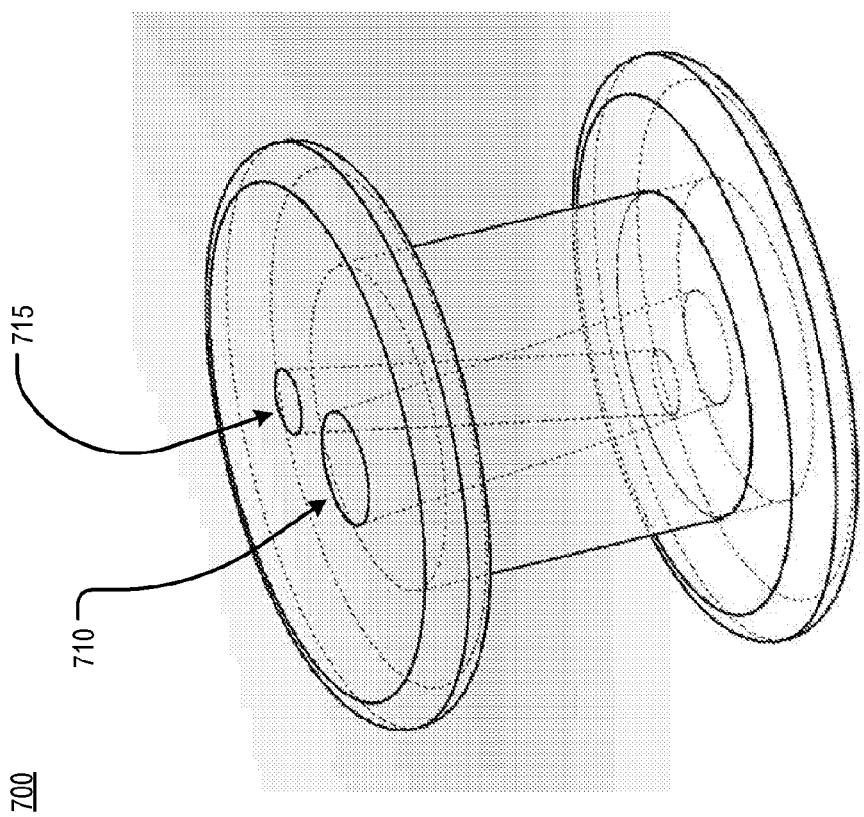
FIG. 7A is a schematic featuring one or more working channels of an apparatus for accessing a pericardial space, according to an exemplary embodiment of the present disclosure.

FIG. 7A and FIG. 7B are illustrations of an access apparatus 700 comprising one or more working channels configured for triangulation of a surgical camera and surgical instruments such that a surgical procedure may be directly visualized. Triangulation of the above-described tools may be accomplished via orientation of one or more working channels within the access apparatus 700. In an embodiment, each of the one or more working channels of the access apparatus 700 extend along a substantially longitudinal axis such that access is provided transcutaneously. In an embodiment, a first working channel 710 is positioned relative to a second working channel 715 such that a relative angle is formed between the two. The relative angle may be defined, in part, by one or more planes encapsulating one or more longitudinal axes of the one or more working channels. In an example, as shown in FIG. 7B, an angle formed between the first working channel 710 and the second working channel 715, housing a camera 722 and a surgical instrument 721, respectively, may form a triangulation angle 724. In an embodiment, and in order to further facilitate observation of the surgical procedure, the surgical camera 722 may be configured with a deflectable lens 723. In another embodiment, the surgical camera 722 may be deflectable or rigid with a set viewing angle large enough to observe the surgical procedure, such as the set viewing angle of an oblique-viewing surgical camera. In an example, the surgical camera 722 may be a deflectable camera with a deflection angle between 0° and 180°.

According to an embodiment of the present disclosure, the triangulation angle 724 may be between 0° and 180°. In another embodiment, the triangulation angle 724 may be between 0° and 25°. In an example, the triangulation angle 724 may be 25°. The triangulation angle 724 may be fixed or may be variable according to the demands of a surgical procedure. In an example, the triangulation angle 724 may be modified from 25° to begin a surgical procedure to 15° by completion of the surgical procedure. Moreover, the triangulation angle 724 may be adjusted before, during, or after use in the surgical procedure.

According to an embodiment, the above-described surgical camera may refer to a camera positioned distal to the access apparatus 700 or may refer to a camera coupled to an endoscope, the endoscope extending through the access apparatus 700 and into the surgical field, and positioned proximal to the access apparatus 700. Surgical camera, camera, and endoscope may, therefore, be used interchangeably to describe a visualization implementation in the present disclosure. Further, it can be appreciated that the above-described visualization implements are merely representative of a variety of implementations providing visualization of a surgical field.

According to an embodiment, the one or more working channels are arranged within the access apparatus 700 such that the first working channel 710 and the second working channel 715 allow for instrument access and visualization of the surgical area. In an embodiment, the first working channel 710 and the second working channel 715 are substantially parallel. In another embodiment, the first working channel 710 and the second working channel 715 are askew.

According to an embodiment, the one or more working channels may be fabricated from a rigid material, a soft material, or a combination thereof, selected from a group including but not limited to polyvinylidene fluoride, polyethylene, polypropylene, polydimethylsiloxane, parylene, polyamide, polytetrafluoroethylene, poly(methyl methacrylate), polyimide, polysiloxane, polyurethane, or a combination thereof. In an embodiment, the one or more working channels may be fabricated from a rigid material in order to secure the orientation of the surgical camera 722 relative to the surgical instrument 721. In another embodiment, the one or more working channels may be fabricated from a soft material such that a user may be granted flexibility, within the context of the triangulation angle 724, in independently moving surgical tools or therapies within the one or more working channels.

Figure 8B:
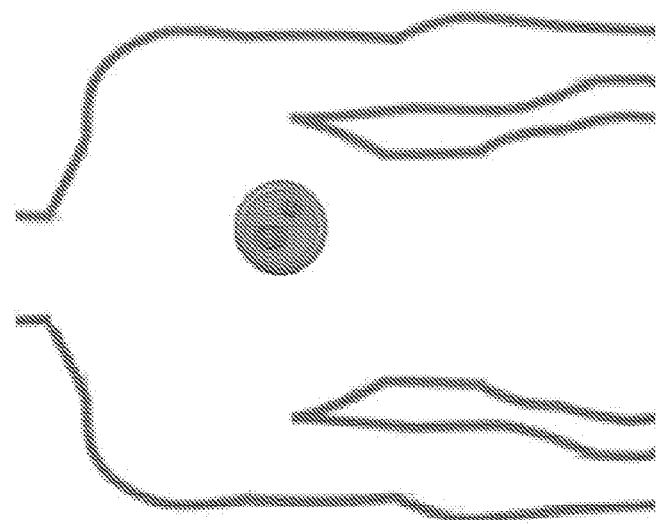
FIG. 8B is an illustration featuring an aspect of an apparatus for accessing a pericardial space, according to an exemplary embodiment of the present disclosure.
Figure 8A:
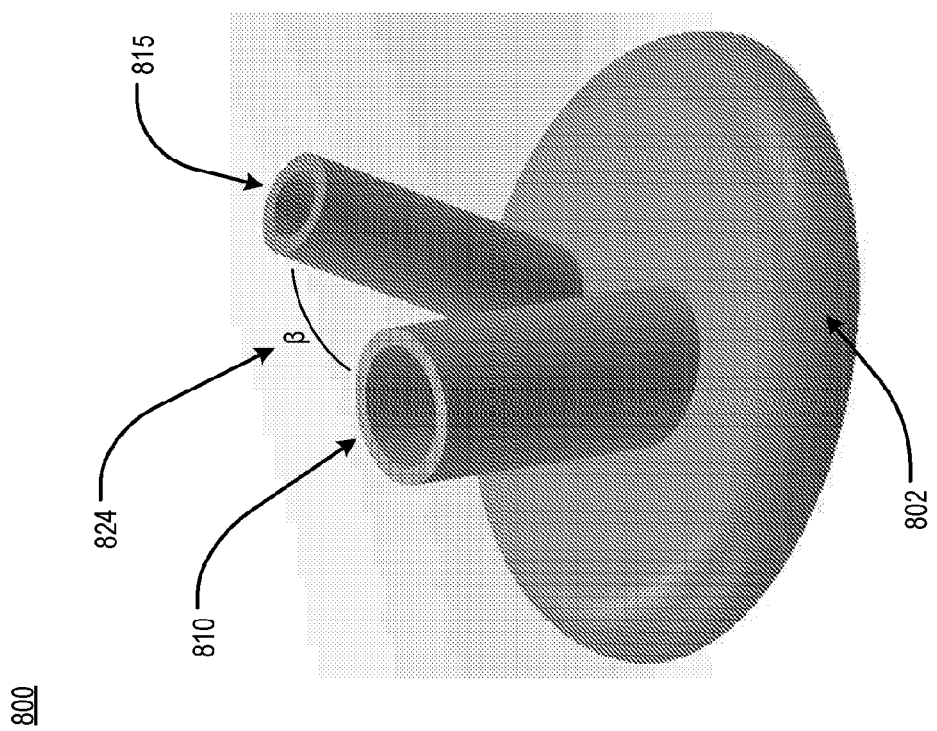
FIG. 8A is an illustration featuring an aspect of an apparatus for accessing a pericardial space, according to an exemplary embodiment of the present disclosure.

According to an embodiment of the present disclosure, the functional arrangement of the one or more working channels may be encapsulated within an extracorporeal apparatus, as shown in FIG. 8A and FIG. 8B. Specifically, an access apparatus 800 may comprise a first working channel 810 and a second working channel 815 disposed on a surface of a proximal flange 802. In an embodiment, the access apparatus 800 may be extracorporeal, as shown in FIG. 8B, wherein each of one or more surgical instruments may be passed through a corresponding one or more working channels in order to penetrate the skin of a patient. To this end, the access apparatus 800 may serve as a guide in order to direct each of the one or more surgical instruments to a correct location within the surgical field to ensure visualization of a surgical field. Further, the one or more working channels may be coupled such that a motion of the first working channel 810 results in a duplicated motion of the second working channel 824, or vice versa. The above-described coupled motion may ensure that a first surgical instrument passed through the first working channel 810 may be continuously visualized by a second surgical instrument passed through the second working channel 815. Alternatively, the one or more channels may not be coupled such that control of the corresponding one or more surgical instruments may be independent.

According to an embodiment of the present disclosure, the first working channel 810 and the second working channel 815 may be arranged such that they may be related by a triangulation angle 824. The triangulation angle 824 may be between 0° and 180°. In another embodiment, the triangulation angle 824 may be between 0° and 25°. In an example, the triangulation angle 824 may be 25°.

Implementing Surgical Instruments of Varied Geometry i. Modular Working Channels According to an embodiment of the present disclosure, an ideal access apparatus may have the capacity to accommodate surgical instruments, visualization tools, and medical therapies of a variety of shapes and sizes.

With reference again to FIG. 1A and FIG. 1B, in an exemplary embodiment, an access apparatus may comprise one or more working channels having a corresponding one or more diameters. The corresponding one or more diameters of the one or more working channels provide flexibility to a user regarding surgical instrument selection. In an embodiment, the one or more working channels may be sized according to a dimension of a largest predicted therapy, wherein, via an additive approach, the access apparatus may further comprise features configured to reduce the dimensions of the one or more working channels, when appropriate. To this end, in an exemplary embodiment, the access apparatus may further comprise one or more plugs coupled to a corresponding one or more tethers, wherein the one or more plugs are of varying dimension such that, when inserted within a corresponding one of the one or more working channels, a diameter of a working channel is reduced. In an embodiment, one or more plugs may be tethered to the access apparatus. In another embodiment, the diameter of the one or more working channels may be reduced by another mechanism including but not limited to a one-way valve, a silicone insert, or other compliant material, or a shape-memory alloy such as nitinol.

Moreover, the one or more working channels may be sized according to a dimension of a smallest predicted therapy, wherein the access apparatus further comprises features to increase the dimensions of the one or more working channels. In an embodiment, the above-described approach may be integrated into the access apparatus, tethered to the access apparatus, or implemented as a standalone component compatible for use with the access apparatus.

ii. Device Breakaway Features

In another, exemplary embodiment, an access apparatus may have a feature allowing the access apparatus to separate into components, via a reductive approach, wherein the component separation increases a dimension of one of the one or more working channels or otherwise improves functionality of the access apparatus. Component separation may occur prior to, during, or following a surgical procedure. Specifically, component separation may allow use of a surgical instrument or surgical therapy substantially larger than either of the one or more working channels, for example, a leadless pacemaker or similarly sized medical device. Alternatively, component separation may be used to remove the access apparatus from the patient following implantation of a surgical instrument.

To this end, FIG. 9A and FIG. 9B is an illustration of a component separation feature, wherein a core is configured to separate from a shell 903 of an access apparatus 900. According to an exemplary embodiment of the present disclosure, through separation of the core 905 from the shell 903 of the access apparatus 900, a modular working channel 935 of substantially increased dimensions may be created from a first working channel 910 and a second working channel 915. The modular working channel 935, as shown in FIG. 9B, may be configured to permit utilization of surgical instruments or surgical therapies of increased dimensions including but not limited leadless pacemakers or other similarly sized cardiac therapies.

According to an embodiment, the core 905 of the access apparatus 900 may be fabricated from a rigid material, a soft material, or a combination thereof. In an embodiment, the core 905 may be fabricated from a rigid material selected from a group including but not limited to polyvinylidene fluoride, polyethylene, polypropylene, polydimethylsiloxane, parylene, polyamide, polytetrafluoroethylene, poly (methyl methacrylate), polyimide, and polyurethane, wherein the rigid material is configured to separate in order to expose one or more modular working channels 935.

In another embodiment, the core 905 may be fabricated from a soft material selected from a group including but not limited to rubber, polysiloxane, and polydimethylsiloxane, wherein the soft material is configured to be turn or cut in order to expose one or more modular working channels 935. In an example, the core 905 may fit entirely within the shell 903, as shown in FIG. 9A, or may be comprised of one or more features, including but not limited to a proximal flange, to prevent the core 903 from being pressed through the shell 905 as surgical instruments are passed through the one or more working channels of the access apparatus 900.

According to another embodiment, and as shown in FIG. 10A and FIG. 10B, an access apparatus 1000 may comprise a coupling mechanism for control of component separation. The coupling mechanism may be selected from a group including but not limited to key and hole, wherein one or more sets of keys and sets of holes, disposed on an internal surface of the access apparatus 1000, may be coupled in order to prevent component separation. In an embodiment, one or more holes 1027 and one or more keys 1028 may be disposed on an internal surface of the access apparatus 1000, as shown in FIG. 10B. The one or more keys 1028 may be configured to couple with the one or more holes 1027. In an example, the one or more keys 1028 and the one or more holes 1027 may be substantially cylindrical and configured for a frictional fit.

In an exemplary embodiment, a force may be applied to an extracorporeal surface of the access apparatus 1000 having a first working channel 1010 and a second working channel 1015, thus separating the access apparatus 1000 into two components along a division line 1026 and exposing the longitudinal dimension of the one or more working channels, as shown in FIG. 10A. In another exemplary embodiment, the access apparatus 1000 may be configured to hinge along a substantially longitudinal axis of the access apparatus 1000. Moreover, the access apparatus 1000 may be configured such that, following component separation, the access apparatus 1000 may be reassembled, as needed. Alternatively, a separation process may be a destructive process such that the components of the access apparatus 1000 may not be rejoined.

According to an embodiment, the access apparatus 1000 may be fabricated from a rigid material, a soft material, or a combination thereof, selected from a group including but not limited to polyvinylidene fluoride, polyethylene, polypropylene, polydimethylsiloxane, parylene, polyamide, polytetrafluoroethylene, poly(methyl methacrylate), polyimide, polysiloxane, polyurethane, or a combination thereof.

Figure 11:
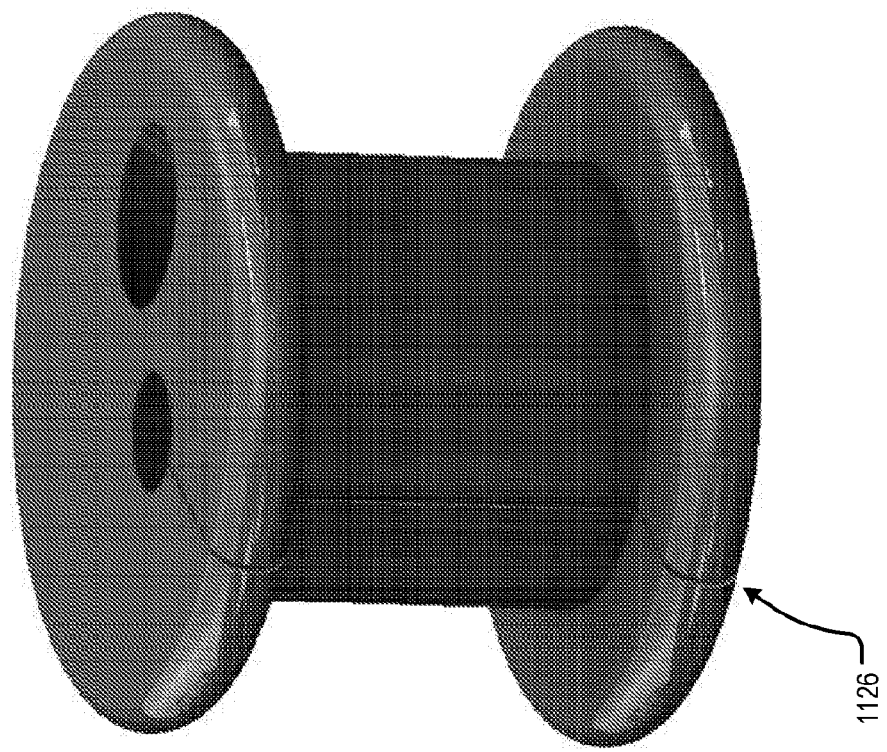
FIG. 11 is an illustration featuring a dividing line of an apparatus for accessing a pericardial space, according to an exemplary embodiment of the present disclosure.
Figure 12A:
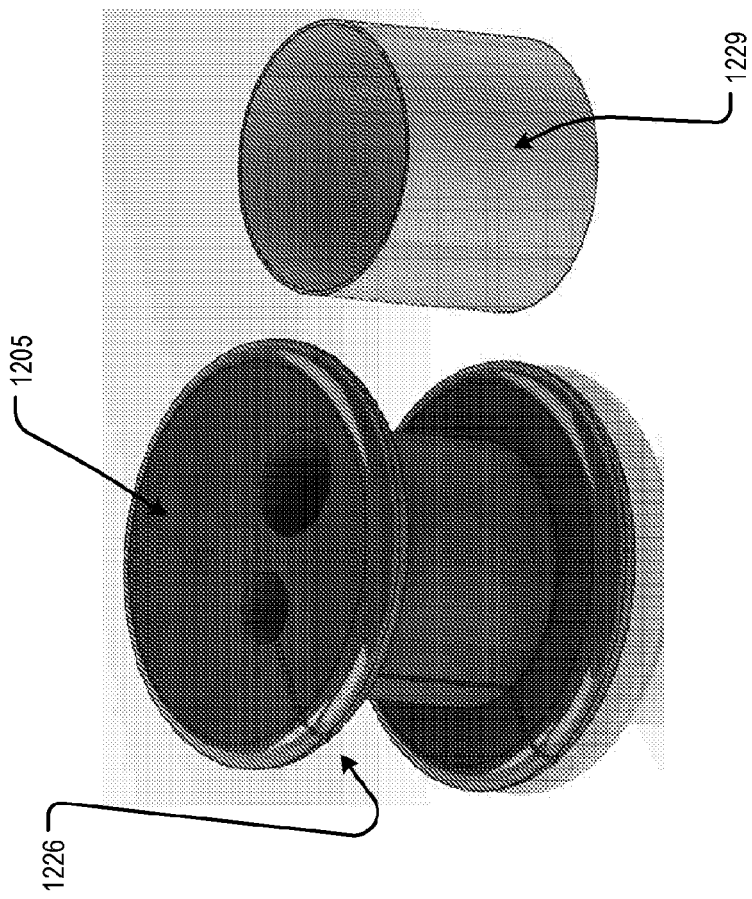
FIG. 12A is an illustration featuring a dividing line and retaining ring of an apparatus for accessing a pericardial space, according to an exemplary embodiment of the present disclosure.
Figure 12B:
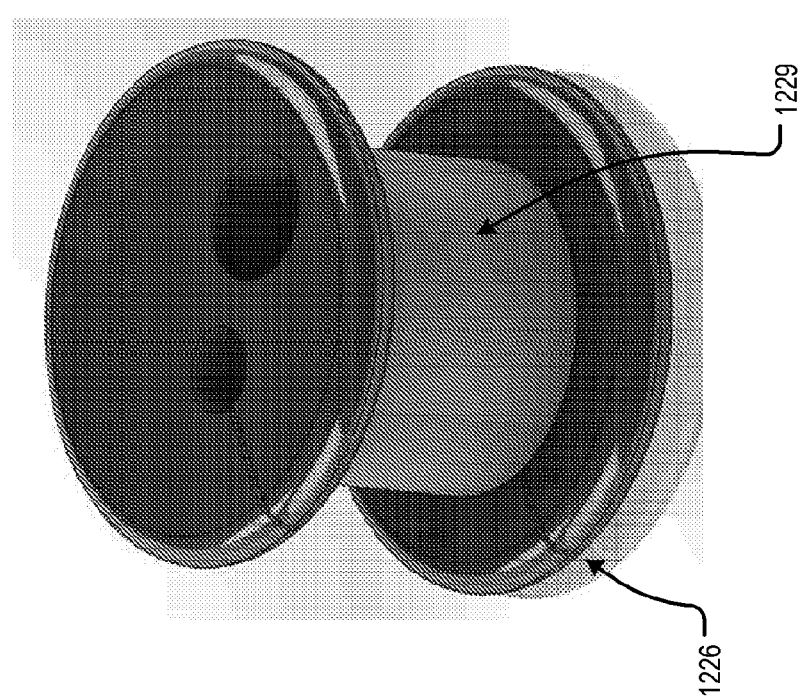
FIG. 12B is an illustration featuring a dividing line and retaining ring of an apparatus for accessing a pericardial space, according to an exemplary embodiment of the present disclosure.

According to another embodiment, the access apparatus may comprise one or more division lines 1126, as shown in FIG. 11. In an example, a division line 1126 may be a perforation in a side of an access apparatus 1100, allowing the access apparatus 1100 to be separated into more than one component along the division line 1126. In another example, as shown in FIG. 11, the division line 1126 may be a physical slit formed in the access apparatus 1100. In an embodiment, wherein the division line 1126 is a physical slit, the access apparatus 1100 may be fabricated from a rigid material, a soft material, or a combination thereof, selected from a group including but not limited to polyvinylidene fluoride, polyethylene, polypropylene, polydimethylsiloxane, parylene, polyamide, polytetrafluoroethylene, poly (methyl methacrylate), polyimide, polysiloxane, polyurethane, or a combination thereof. In an example, the access apparatus 1100 may be fabricated from a rigid material and the division line 1126 may extend through a sufficient length of the access apparatus 1100 such that a force applied by a hand, a surgical tool, or other mechanism, may be sufficient to separate the access apparatus 1100 into a plurality of components. In another example, the access apparatus 1100 may be fabricated from a soft material and a retaining mechanism, as shown in FIG. 12A and FIG. 12B, may be used to prevent separation of the plurality of components of the access apparatus 1200 under applied force, allowing surgical instruments to pass through. To this end, the retaining mechanism, a retaining ring 1229, maintains structural rigidity of the access apparatus 1200 during insertion of a surgical instrument. Further, FIG. 12B illustrates a core 1205 of the access apparatus 1200 wherein the retaining ring 1229 may be positioned circumferentially such that the access apparatus 1200 does not separate along a division line 1226.

Figure 13B:
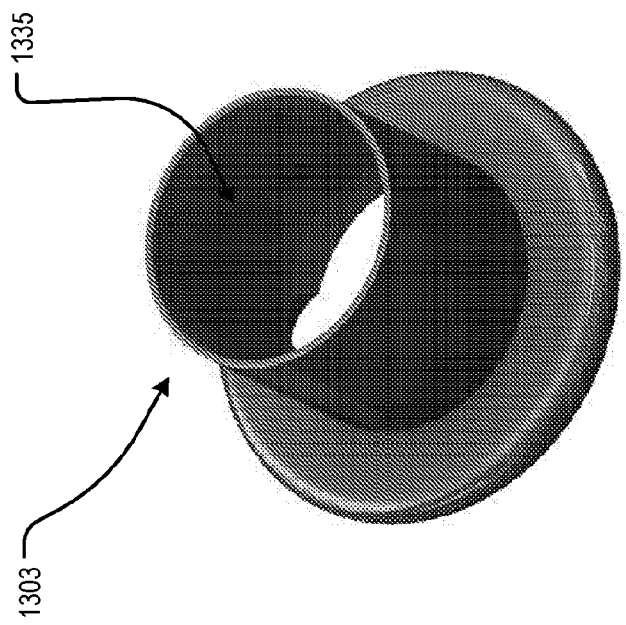
FIG. 13B is an illustration of a separating feature of an aspect of an apparatus for accessing a pericardial space, according to an exemplary embodiment of the present disclosure.
Figure 13A:
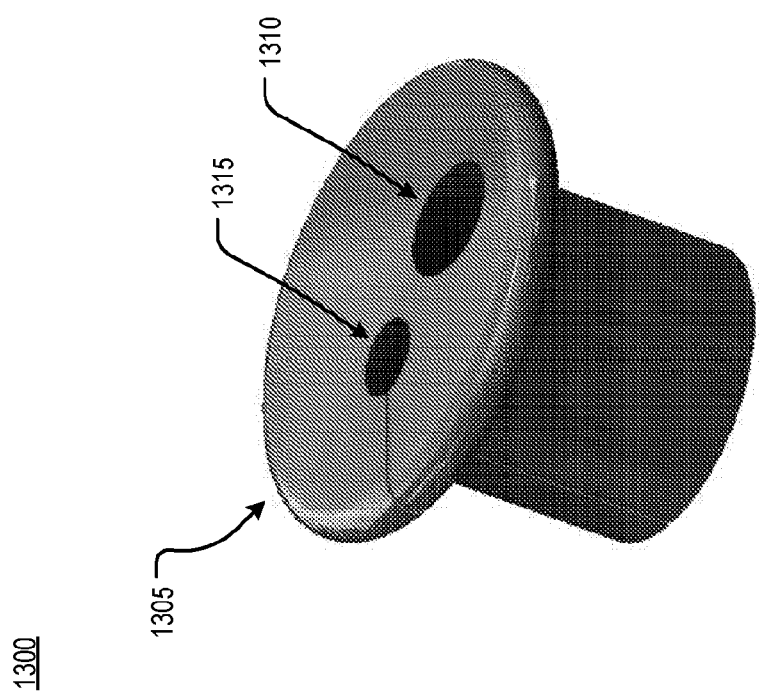
FIG. 13A is an illustration of a separating feature of an aspect of an apparatus for accessing a pericardial space, according to an exemplary embodiment of the present disclosure.

According to another embodiment of the present disclosure, an access apparatus 1300 may be fabricated such that a plurality of components may be separated via pulling. As shown in FIG. 13A and FIG. 13B, the access apparatus 1300 may comprise a core 1305 and a shell 1303. Upon insertion of the access apparatus 1300, standard surgical instruments and surgical cameras may be introduced to the surgical window via a first working channel 1310 and a second working channel 1315 disposed within the core 1305. In so much as a larger dimension surgical instrument need be used, the core 1305 may be pulled apart from the shell 1303, thus exposing a modular working channel 1335 able to accept larger therapies or other implantable therapies such as a leadless pacemaker. In an example, during an initial phase of a surgical procedure for implanting a leadless pacemaker, the first working channel 1310 and the second working channel 1315 may be utilized in order to access the pericardial space. Once accessed, the core 1305 of the access apparatus 1300 may be removed such that a leadless pacemaker may be inserted into the pericardial space modular working channel 1335.

Obtaining Pericardial Access

Figure 14:
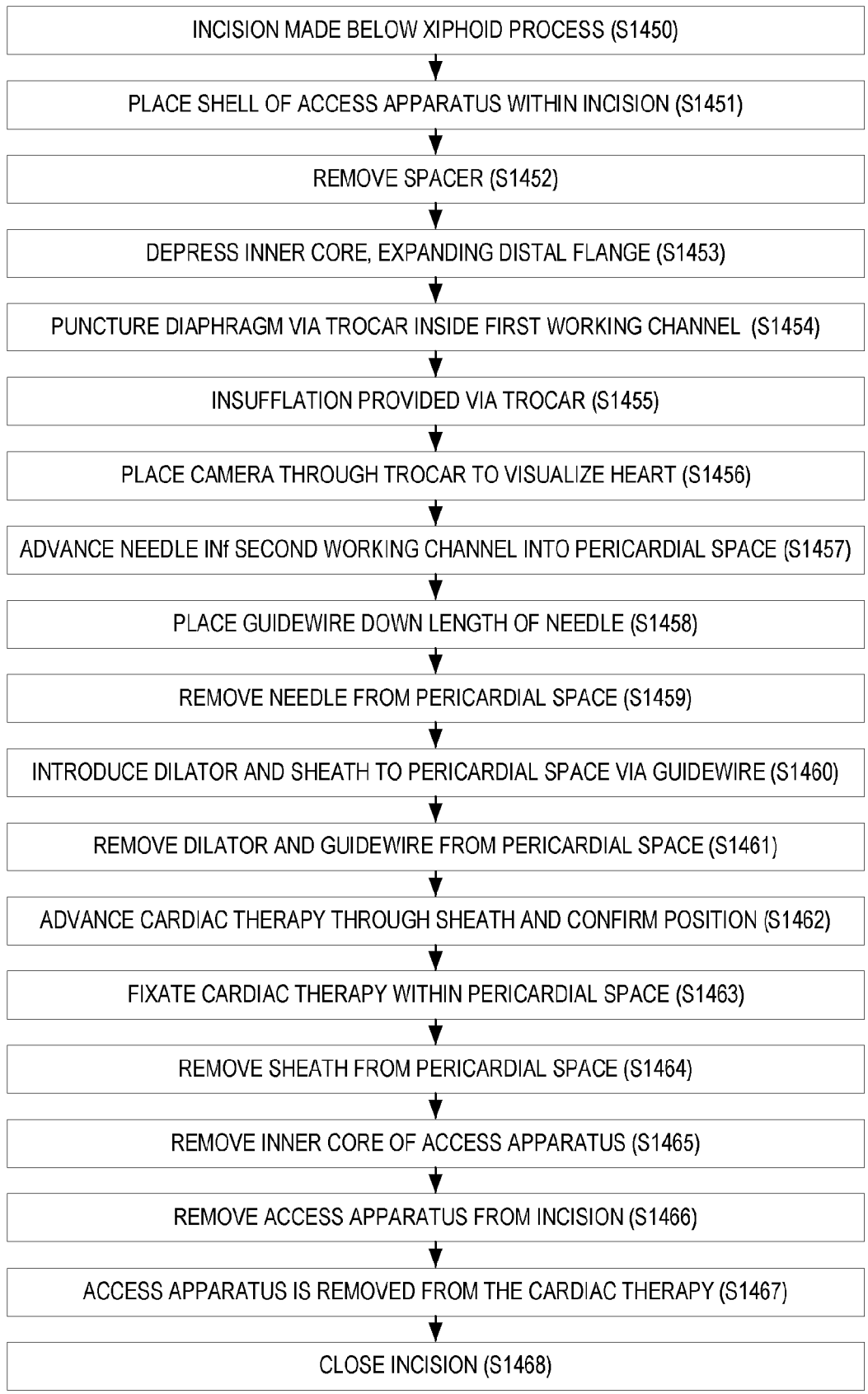
FIG. 14 is a flowchart of a clinical workflow for using an apparatus for accessing a pericardial space, according to an exemplary embodiment of the present disclosure.

The above-described access apparatus may be used for delivery therapies to the heart wherein access to the pericardial space must be gained. To this end, FIG. 14 describes a process by which the pericardial space may be accessed, and a medical therapy implanted, via implementation of an embodiment of the access apparatus of the present disclosure, with reference to FIG. 1A and FIG. 1B. First, an incision may be made below the xiphoid process of the patient S1450, a cartilaginous tissue at an inferior aspect of the sternum in developing humans. Next, the rigid shell of the access apparatus may be positioned within the incision S1451. Following removal of the spacer of the access apparatus S1452, the core of the access apparatus may be depressed, thus deploying the distal flange S1453 or, in an embodiment, a mutable flange. A trocar may then be passed through a larger, first working channel of the access apparatus and used to puncture the diaphragm of the patient S1454. Insufflation may then be provided through the trocar to create a surgical volume S1455. Next, a camera may be placed down the trocar and used to visualization the heart of the patient S1456. A needle may passed through the second working channel of the access apparatus and advanced into the pericardial space of the heart S1457. A guidewire may then be passed down the needle S1458, thus allow the needle to be removed from the pericardial space S1459. Via the guidewire, a dilator and sheath may be passed into the pericardial space S1460. With the sheath in position, the dilator and guidewire may be removed from the pericardial space S1461. A medical therapy or, for instance, cardiac therapy, may be advanced through the sheath and positioned within the pericardial space, as confirmed via direct visualization S1462. The cardiac therapy may then be fixated within the pericardial space S1463. Once implanted, the sheath may first be removed from the pericardial space S1464, followed by removal of the core of the access apparatus from the shell via force exerted on a proximal flange of the access apparatus S1465. Lastly, the shell of the access apparatus may be removed from the patient S1466, the access apparatus may be removed from the patient S1467 and the incision may be closed S1468.

The above-described implementation of an embodiment of the access apparatus for delivery of a medical therapy employs a process that, with modification, may be applied to a variety of processes. Specifically, and in order to minimize risk, the process of FIG. 14, with modification, may be applied to increasingly minimally-invasive therapies.

Figure 15A:
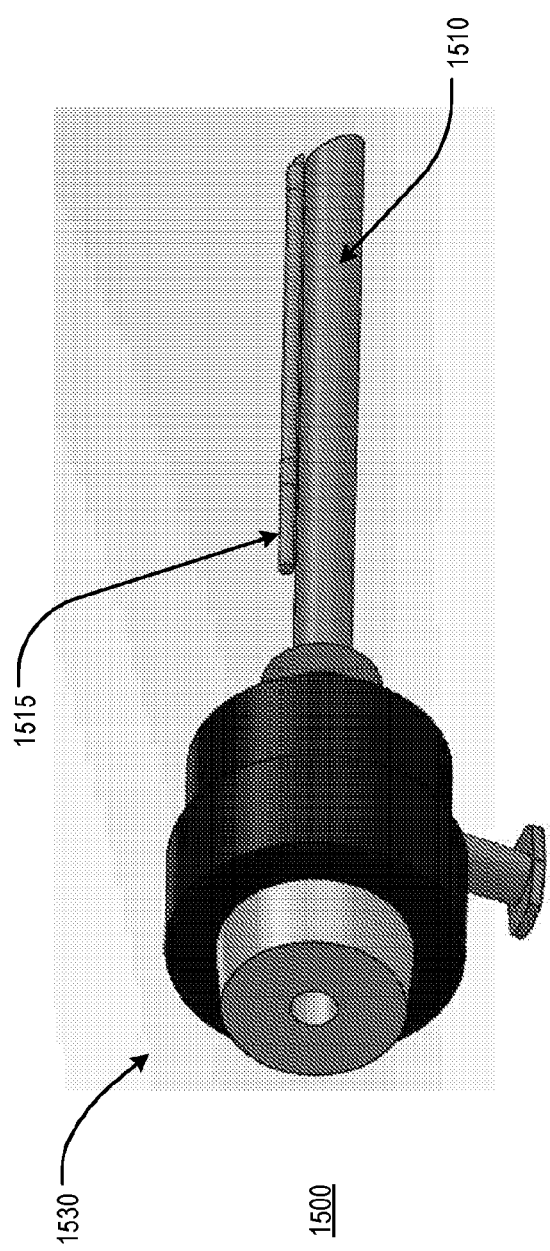
FIG. 15A is an illustration featuring one or more working channels of an apparatus for accessing a pericardial space, according to an exemplary embodiment of the present disclosure.
Figure 15B:
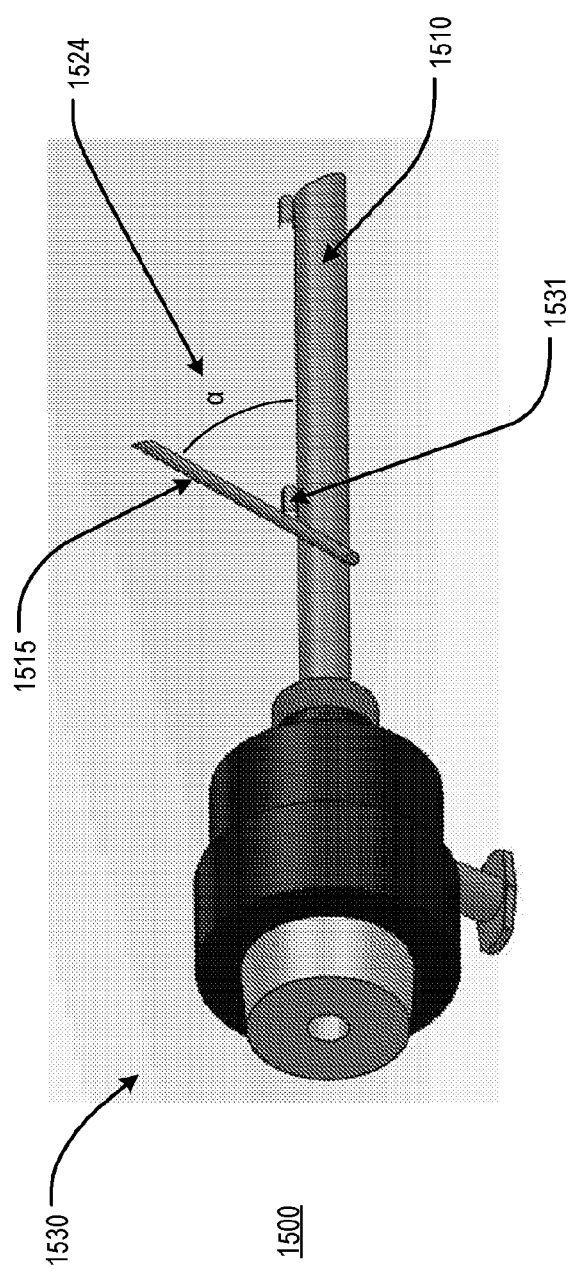
FIG. 15B is an illustration featuring one or more working channels of an apparatus for accessing a pericardial space, according to an exemplary embodiment of the present disclosure.

According to an embodiment, and in order to, for example, deliver certain cardiac therapies to the surgical field, a minimally-invasive, percutaneous approach may be used. To this end, as shown in FIG. 15A and FIG. 15B, an access apparatus 1500 may comprise one or more working channels coupled via a pin 1531, or hinge, disposed at a distance from a trocar 1530. In an embodiment, the pin 1531 is disposed at a distance from the trocar 1530 along a surface of a first working channel 1510 adjacent to a second working channel 1515. As a result of this coupling, and the functionality pursuant therefrom, the second working channel 1515 and the first working channel 1510 may be moved simultaneously. Concurrently, surgical instruments or surgical therapies inserted through the one or more working channels may be utilized and moved independently. Moreover, and in order to provide triangulation of a surgical instrument with, for instance, a camera inserted through the first working channel 1510, the second working channel 1515 may be angulated from the first working channel 1510, about the pin 1531, by a triangulation angle 1524. The triangulation angle 1524 may be adjusted in order to accommodate visualization of a variety of surgical therapies and surgical instruments.

According to an embodiment, and in order to achieve the triangulation angle 1524, the location of the pin 1531 may be moved proximally or distally along the length of the first working channel 1510. In another embodiment, the pin 1531 may be locked such that any of a variety of angles of the triangulation angle 1524 may be achieved.

In an exemplary embodiment, the first working channel 1510 and the second working channel 1515 may be arranged about the pin 1531 such that the triangulation angle 1524 may be between 0° and 180°. In another embodiment, the triangulation angle 1524 may be between 0° and 25°. In an example, the triangulation angle 1524 may be 25°.

Figure 16A:
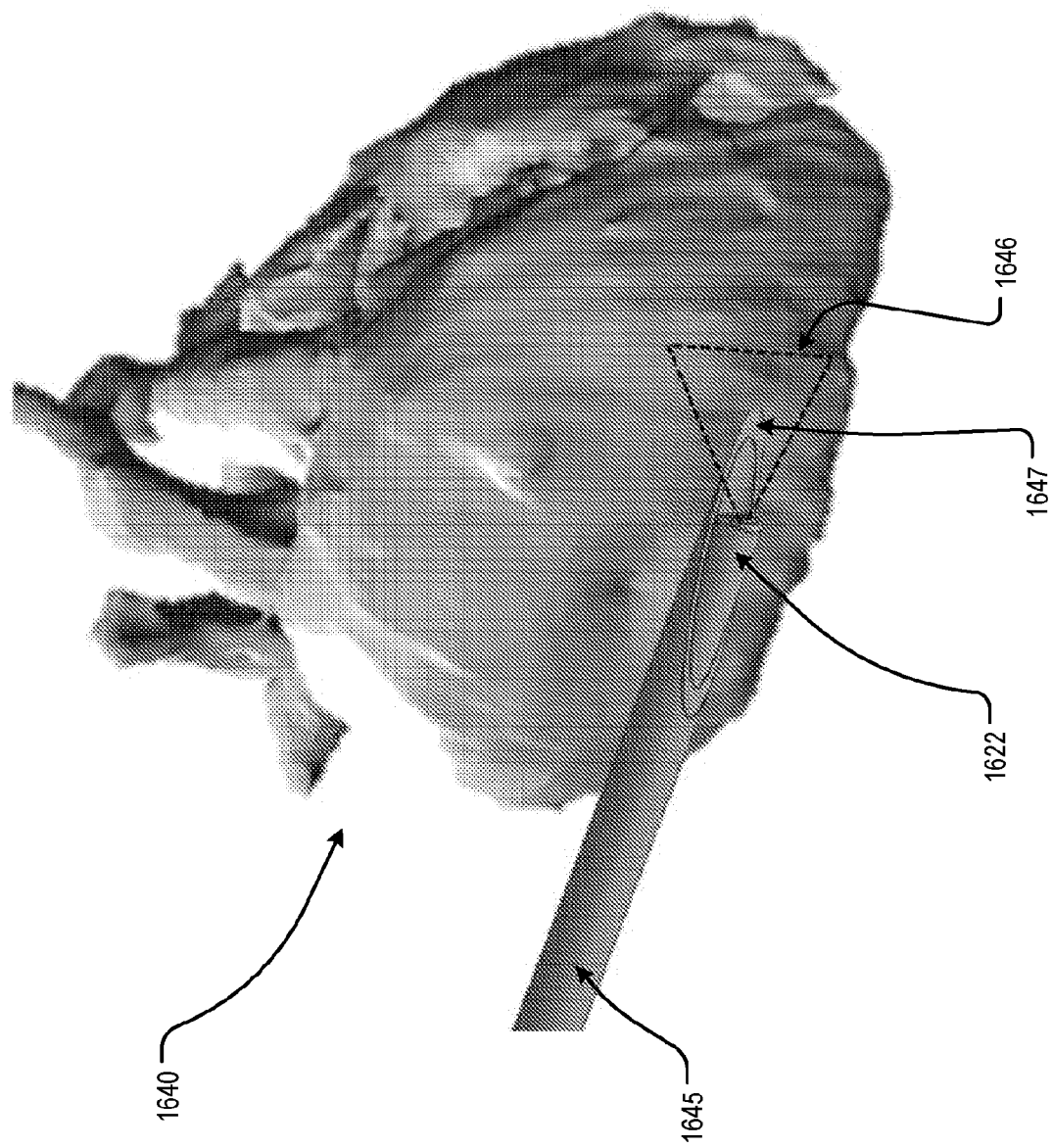
FIG. 16A is an illustration of an implementation of an apparatus for accessing a pericardial space, according to an exemplary embodiment of the present disclosure.
Figure 16B:
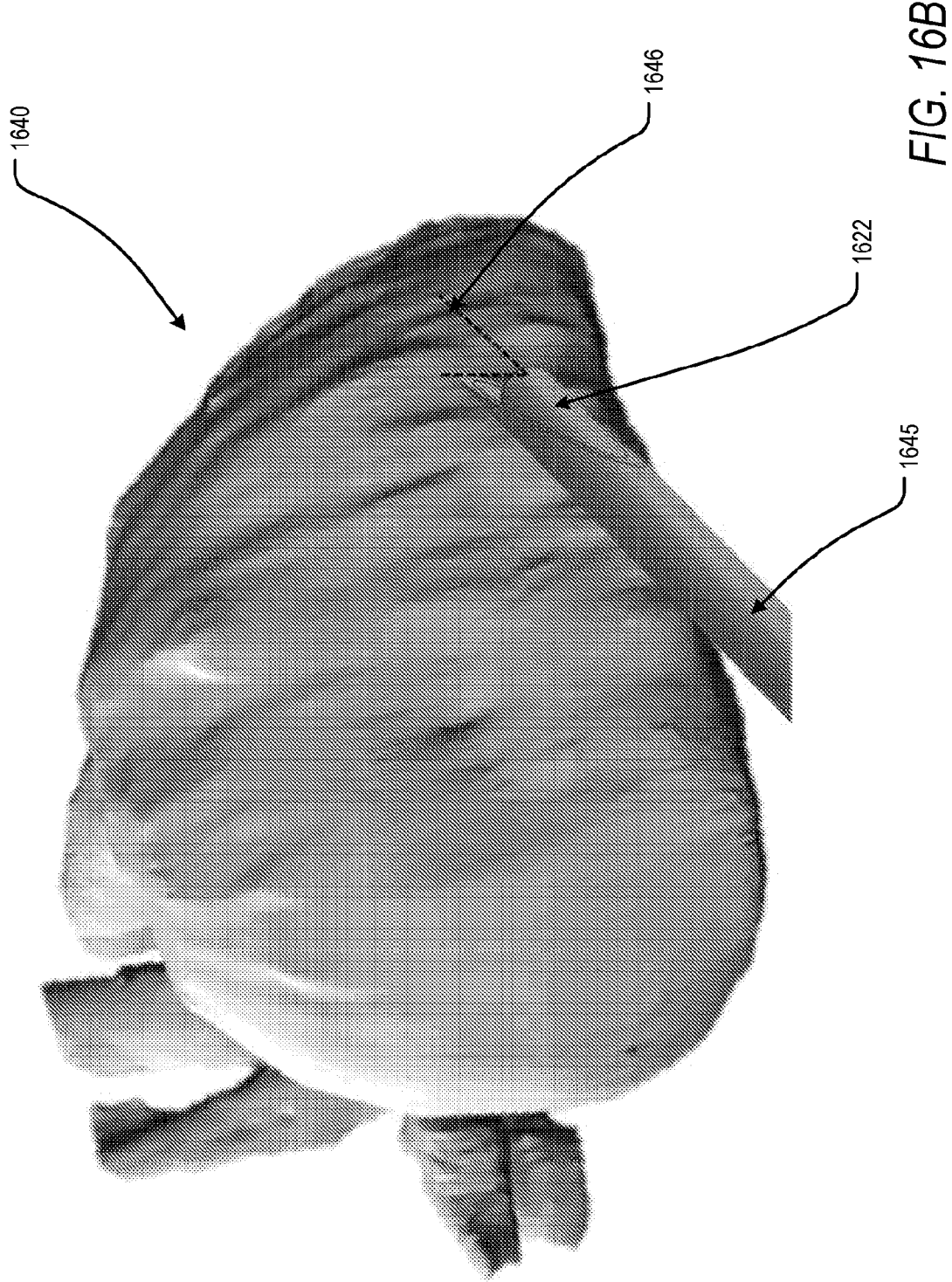
FIG. 16B is an illustration of an implementation of an apparatus for accessing a pericardial space, according to an exemplary embodiment of the present disclosure.
Figure 16C:
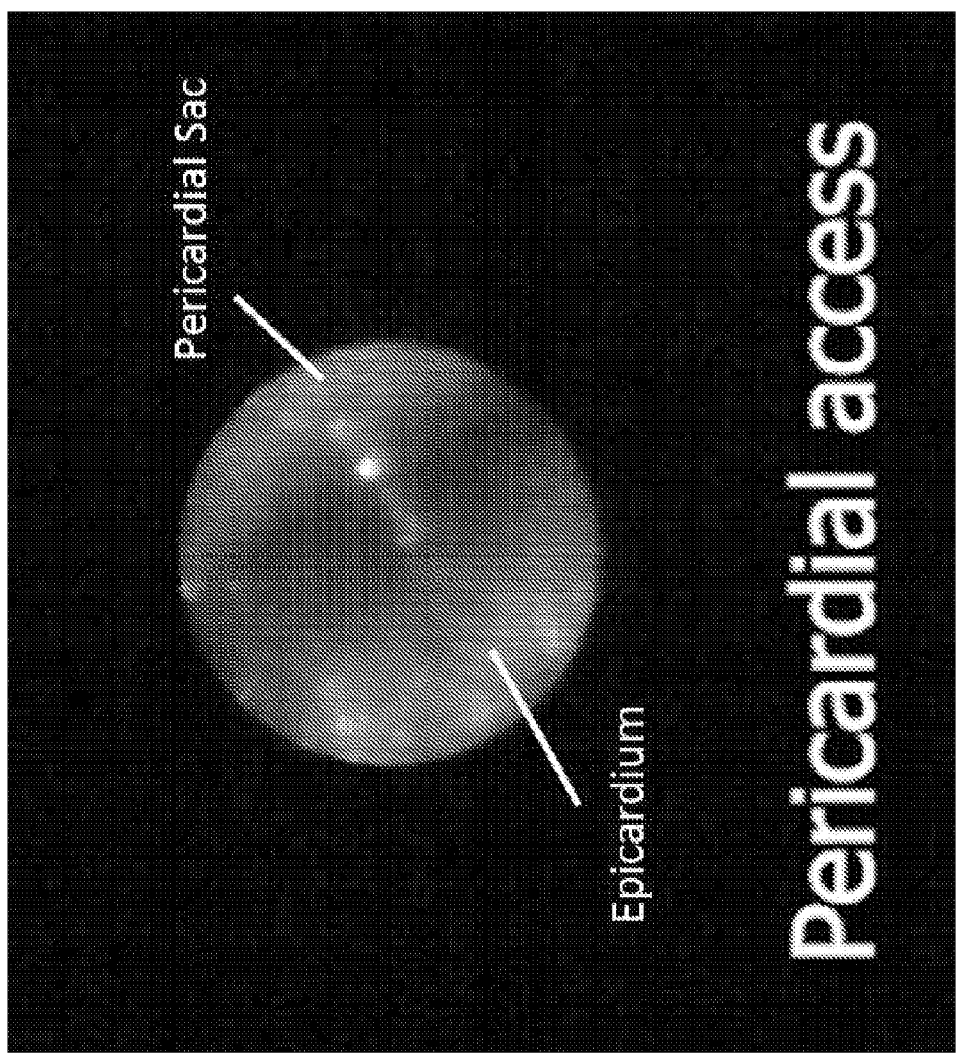
FIG. 16C is a graphical illustration of a visualization of a pericardial sac of a patient, according to an exemplary embodiment of the present disclosure.

Following insertion of a camera through a trocar, and, for instance, positioning a second working channel relative to a first working channel for visualization of the surgical field, the pericardial space may be accessed. In a generic embodiment, and as shown in FIG. 16A, FIG. 16B, and FIG. 16C, the pericardial space may accessed via coaxially-positioned needle 1645 and camera 1622 via an access apparatus. The camera 1622 may be a rigid, flexible, or deflectable camera with a fixed or adjustable viewing angle 1648, as shown in FIG. 16B, of between 0° and 90°, in order to view the needle 1645 within the surgical field.

According to an embodiment, and in order to access the pericardial space, the needle 1645 may first be placed through the access apparatus. Next, the camera 1622 may be placed within the needle 1645 and adjusted to a depth such that a safe access tip 1647 of the needle 1645 may be visualized within the surgical field of view 1646. FIG. 16C is a graphical illustration of the surgical field of view, and pericardial sac therein, as visualized via the camera. A locking feature may fix the position of the camera 1622 relative to the needle 1645. Once fixed, the needle 1645 may be advanced in order to puncture the pericardial sac of a heart 1640 and be inserted in to the pericardial space. The safe access tip 1647 of the needle 1645 ensures puncture of the pericardial sac without rupture of the epicardial surface. According to an embodiment, the safe access tip 1647 is fabricated from a soft, compliant material. In another embodiment, the safe access tip 1647 is outfitted with a tactile sensor, coupled to necessary processing circuitry, to determine a force applied to the safe access tip 1647 and to prevent force application at a level which may penetrate the epicardial surface of the heart 1640. The camera 1622 may then be removed and a guidewire may be inserted through the needle 1640 and placed within the pericardial space. Via the Seldinger technique, surgical therapies, such as leadless pacemakers, may be delivered to the pericardial space over the inserted guidewire.

According to an embodiment, the above-described camera may refer to a camera positioned distal to the access apparatus or may refer to a camera coupled to an endoscope, the endoscope extending through the access apparatus and into the surgical field, and positioned proximal to the access apparatus. Surgical camera, camera, and endoscope may, therefore, be used interchangeably to describe a visualization implementation in the present disclosure. Further, it can be appreciated that the above-described visualization implements are merely representative of a variety of implementations providing visualization of a surgical field.

Further to the above-described generic embodiment, a variety of percutaneous approaches for delivering cardiac therapies while providing direct visualization may be implemented. As a result, access to the pericardial space may be gained while eliminating incisions, thus enhancing safety and procedural efficacy. Each of the below-described approaches are grounded in the importance of visualization and confirming, during a surgical procedure, the location of surgical instruments including but not limited to sheaths and dilators, thereby reducing the risks of heart puncture and improving lead fixation at the heart apex.

Figure 17:
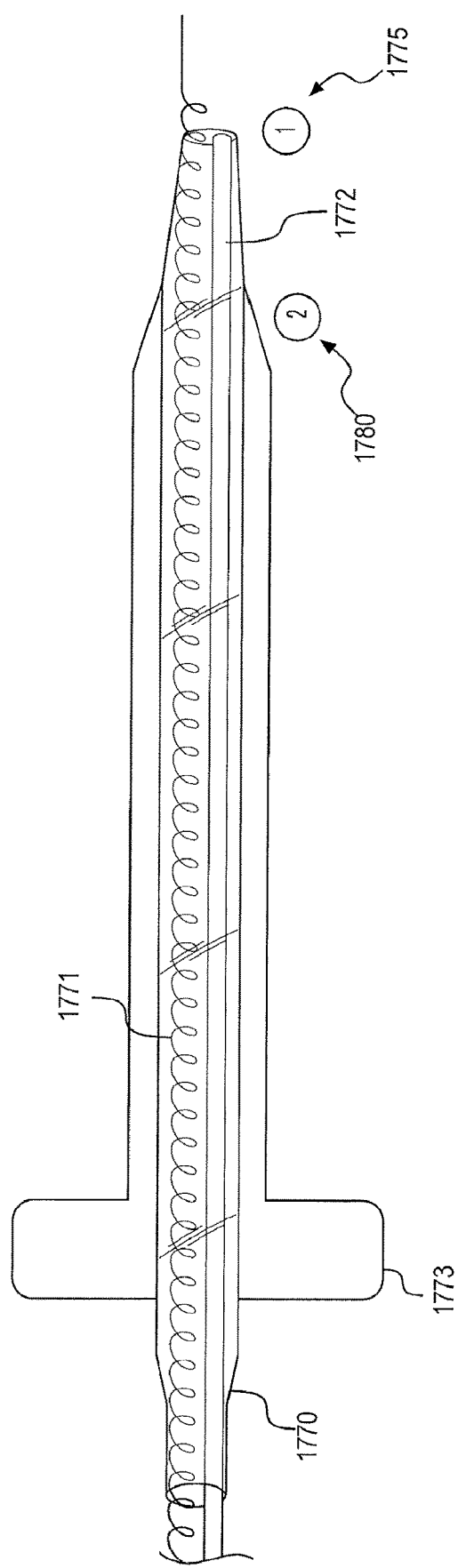
FIG. 17 is a schematic of a camera and a guidewire within a lumen of a dilator, according to an embodiment of the present disclosure.
Figure 18:
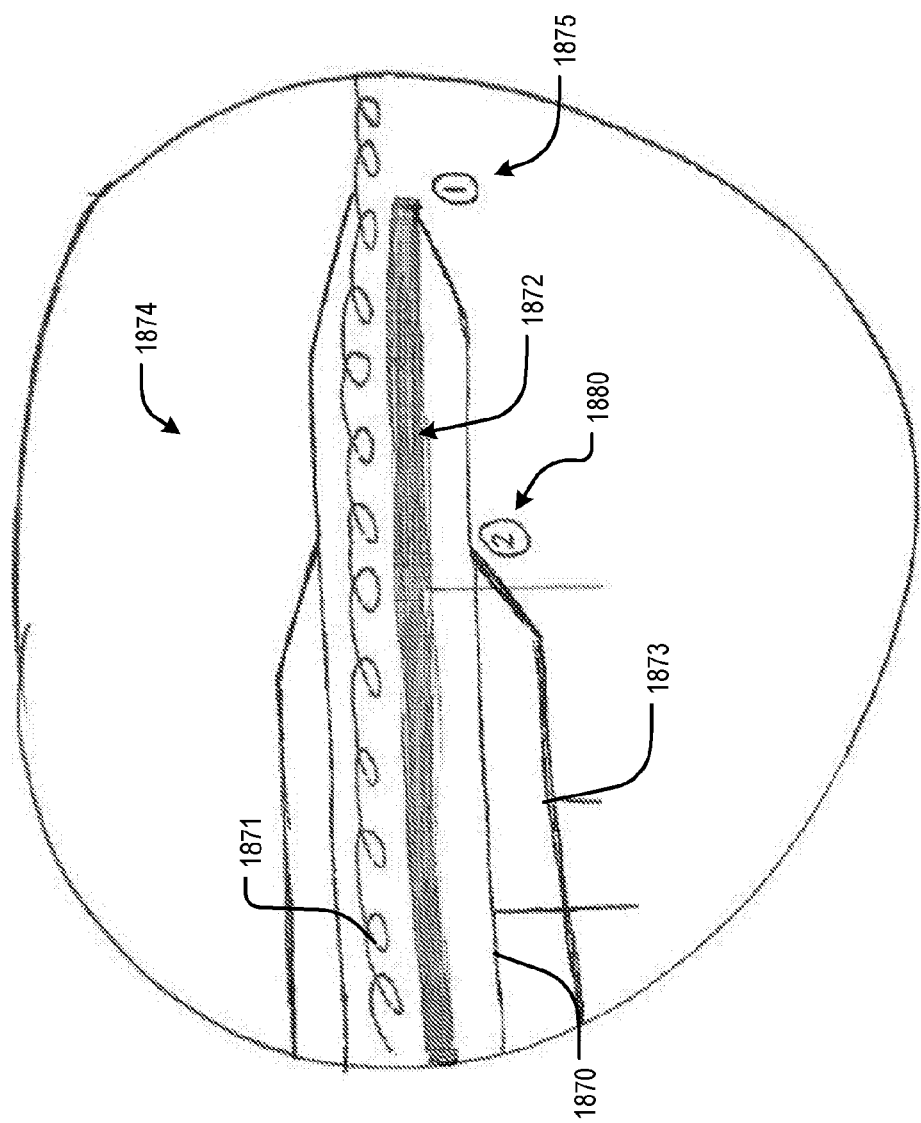
FIG. 18 is a schematic of a camera at a first position, wherein a view of a surgical field is provided from a tip of a dilator, according to an exemplary embodiment of the present disclosure.

To this end, and according to an embodiment, FIG. 17 is a schematic of a modified dilator 1770 that may contain a guidewire 1771 and a camera 1772 within a single lumen. The lumen of the dilator 1770 may be separable into a plurality of lumens to allow for the physical separation of the guidewire 1771, the camera 1772, or other tools, either along the entire lumen or at particular segments. After the guidewire 1771 has been inserted into the pericardial space, the dilator 1770 may be pre-marked with locations indicating two different positions. A first position 1775, or Position 1, may indicate when the dilator 1770 is completely through a sheath 1773 and a distal tip of the dilator 1770 is projecting from the sheath 1773, shown in FIG. 18. In the above-described configuration, the camera 1872 is at the distal tip of the dilator 1870 and provides direct visualization and confirmation of the location of the dilator 1870. Position 1 1875 may be the first location that is visualized for the sheath and dilator complex 1874.

Figure 19:
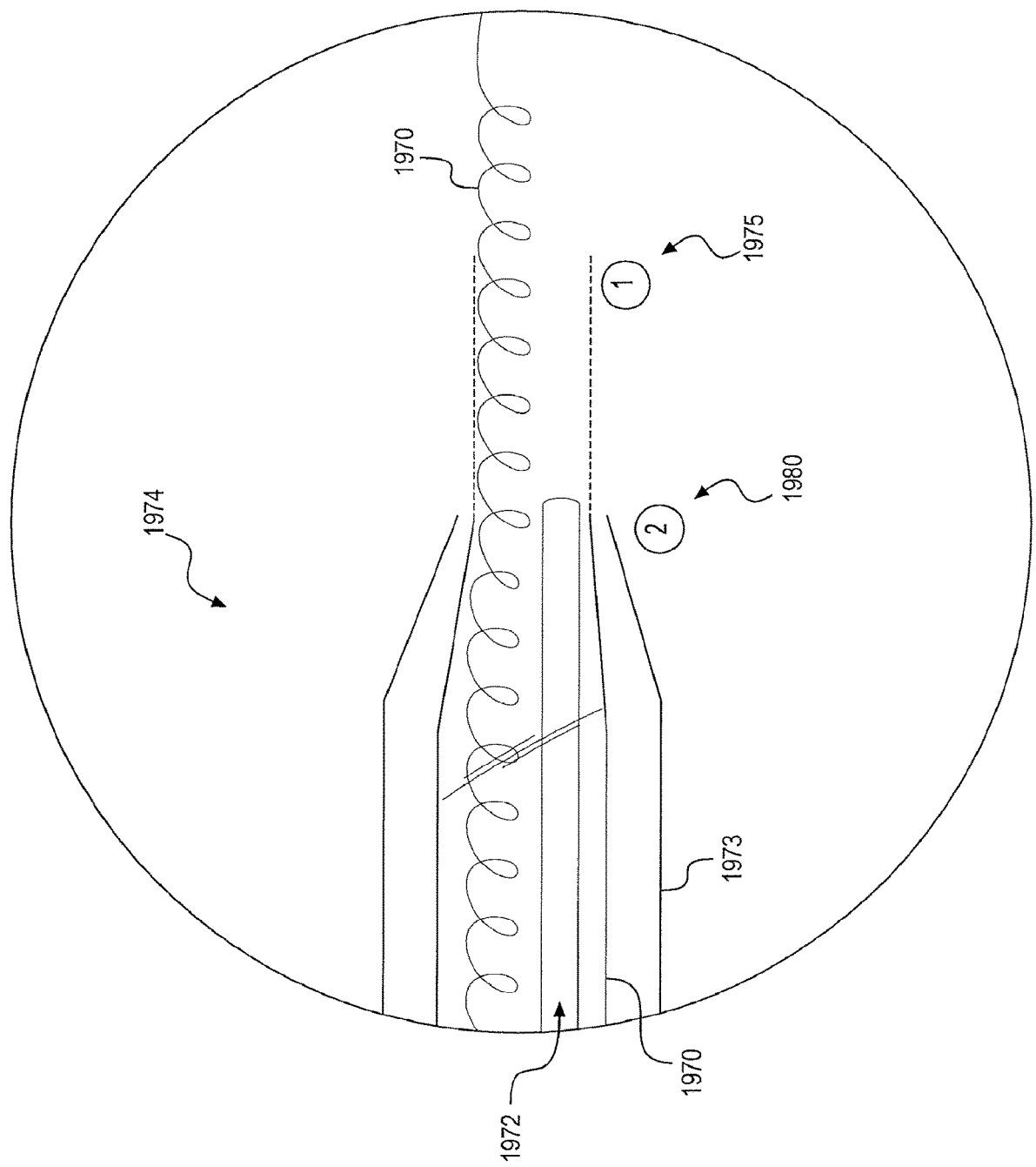
FIG. 19 is a schematic of a camera and a dilator wherein the dilator is at a second position, according to an exemplary embodiment of the present disclosure.

In order to confirm the location of the sheath, the dilator may be moved to a second position 1880, or Position 2, along the guidewire 1871, as shown in FIG. 19. Position 2 1980 is the tip of the narrowest part of the sheath 1973. There may be one or more markings on the dilator 1970 indicating each of the two positions. Furthermore, the sliding mechanism of the dilator 1970 may be facilitated with an adapter or retracting mechanism to move the dilator 1970 from the first position 1975 to the second position 1980. In addition, an adapter or a modification in the sheath and dilator complex 1974 may be used to allow the camera 1972 and the guidewire 1970 to move together or separately.

Throughout the duration of the procedure, visualization may be provided by a camera 1972 within the dilator 1970. As described above, in another embodiment, the camera 1972 may be a camera coupled to an endoscope, the endoscope extending in the surgical field. After confirmation of locations of the sheath 1973 and the dilator 1970, the camera 1972 and the guidewire 1970 may be removed from the pericardial space via retraction of the dilator 1970 from the sheath 1973. The sheath 1973, breakable in an example, may then be used to introduce a pacemaker lead into the heart.

According to an embodiment, the dilator 1970 may be fabricated from a variety of materials including but not limited to stainless steel, polyethylene terephthalate, polyvinylidene fluoride, polyethylene, polypropylene, polydimethylsiloxane, parylene, polyamide, polytetrafluoroethylene, poly(methyl methacrylate), polyimide, polyurethane, or a combination thereof, and may be fabricated via a variety of techniques including but not limited to extrusion molding, blow molding, injection molding, and machining. Similarly, the sheath 1973 may be fabricated from a variety of materials including but not limited to stainless steel, polyethylene terephthalate, polyvinylidene fluoride, polyethylene, polypropylene, polydimethylsiloxane, parylene, polyamide, polytetrafluoroethylene, poly(methyl methacrylate), polyimide, polyurethane, or a combination thereof, and may be fabricated via a variety of techniques including but not limited to extrusion molding, blow molding, injection molding, and machining.

Additional modifications to the dilator 1970 may include changes in the cap and the lumen in order to introduce the camera 1972 into the dilator 1970. In an exemplary embodiment, the camera 1972 may have a different entrance into the lumen via additional branching of the dilator 1970.

Figure 20:
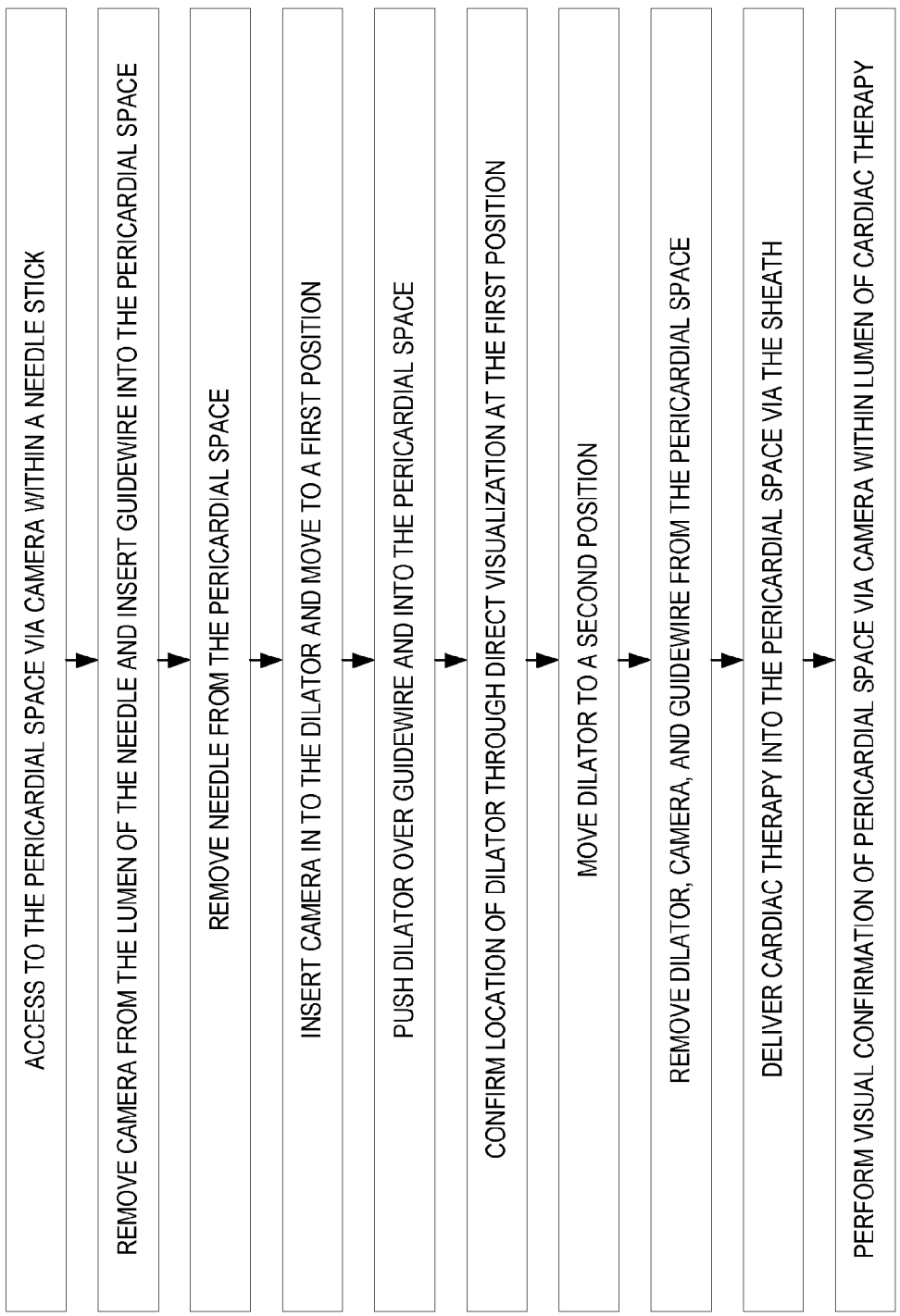
FIG. 20 is a flowchart of pericardial access, according to an exemplary embodiment of the present disclosure.

FIG. 20 is a flowchart of the above-described approach. First, access to the pericardial space may be gained through a camera down a needle stick. The camera may then be removed from the lumen of the needle and a guidewire may be inserted into the pericardial space. After removing the needle from the pericardial space, the camera may be inserted into the dilator and moved to a first position. A dilator and sheath complex may then be pushed over the guidewire and into the pericardial space. The location of the dilator may be confirmed through direct visualization at the first position. Next, the dilator tip may be moved to a second position. The dilator, the camera, and the guidewire may then be removed from the pericardial space, leaving the sheath in position. A cardiac therapy may then be delivered into the pericardial space via the sheath and the position thereof may be visually confirmed via camera within the lumen of the cardiac therapy.

Figure 21:
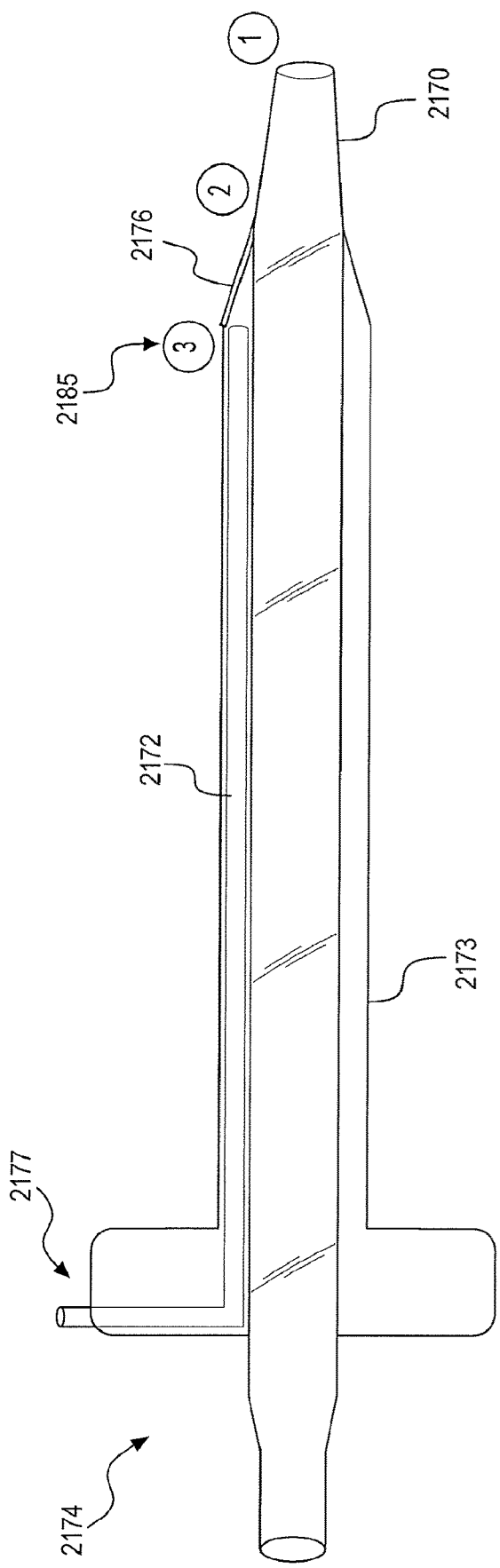
FIG. 21 is a schematic of a camera located between a guidewire and an inner wall of a sheath, according to an embodiment of the present disclosure.

According to another embodiment, the camera for direct visualization may be located within the delivery sheath and external to the dilator, as shown in FIG. 21, and in contrast the embodiment of FIG. 17, wherein the camera must be moved between a first position and a second position for visual confirmation. To this end, an end of a camera 2172 may be placed at an end of a widest portion of a sheath 2173, referred to herein as a third position 2185. A tapering segment of the sheath 2173 may consist of a clear material 2176 or window that allows for the camera 2172 to view a tip of a dilator 2170. Alterations to the tip length of the dilator 2170 may be made to ensure visibility of the tip of the dilator 2170 from the camera 2172 at the third position 2185. Moreover, the tapered segments of the sheath 2173 and the dilator 2170 may be lengthened or shortened to facilitate movement of procedural tools and to ensure proper dilation within the tissues.

In implementing the above-described embodiment, and following gaining access to the pericardial space, guidewire insertion, and needle removal, the camera 2172 may be inserted into the sheath and dilator complex 2174 through an opening 2177 in the side of the sheath 2173. In an example, the camera 2172 may be inserted through the sheath's handle, into additional branches, or extended out of the cap of the dilator 2170. The sheath and dilator complex 2174 may then be introduced into the pericardial space via a guidewire.

Visualization of the tip of the dilator 2170 from the third position 2185 may result in the confirmation of the sheath and dilator complex 2174 within the pericardial space. After the location of the dilator 2170 and the sheath 2173 has been confirmed, the dilator 2170 and guidewire may be removed from the pericardial space. Subsequently, a pacemaker lead may be introduced into the pericardial space via the sheath 2173 and fixated to the heart.

Figure 22:
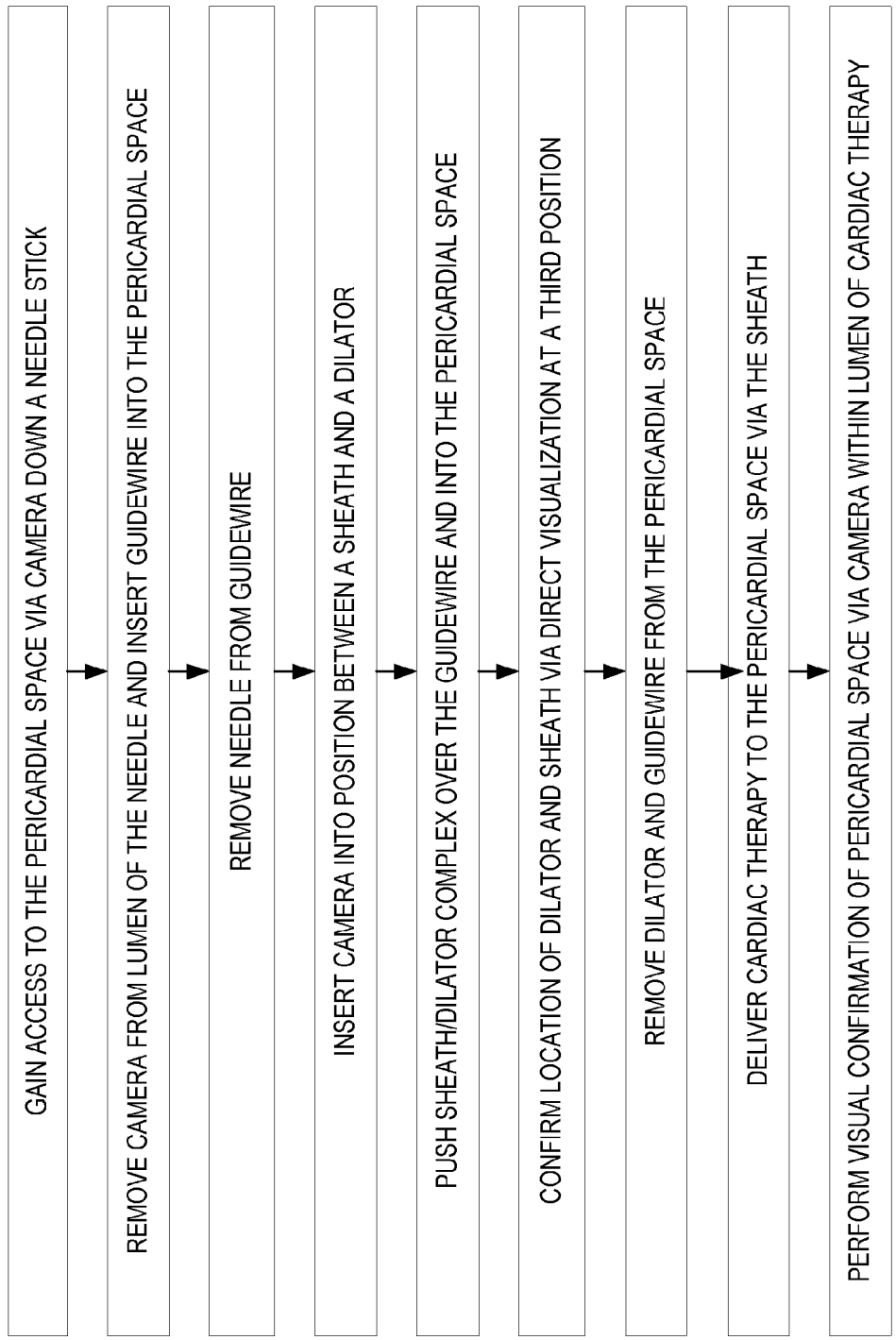
FIG. 22 is a flowchart for gaining pericardial access without visualization, according to an exemplary embodiment of the present disclosure.

FIG. 22 is a flowchart of the above-described approach. First, access to the pericardial space may be gained through a camera down a needle stick. Once access to the pericardial space has been gained, the camera may be removed via the lumen of the needle and replaced by a guidewire inserted into the pericardial space. Once the guidewire is positioned, the needle may be removed. According to FIG. 21, the camera may be inserted into its position within the sheath and dilator complex. The sheath and dilator complex may then be pushed over the guidewire and into the pericardial space. Visual confirmation of the location of the sheath and dilator complex may be performed at the third position. Once confirmed, the dilator and the guidewire may be removed from the pericardial space, thus allowing cardiac therapies to be delivered to the pericardial space via the sheath. Positioning of the cardiac therapy may be visually confirmed via camera within the lumen of the cardiac therapy.

Figure 23:
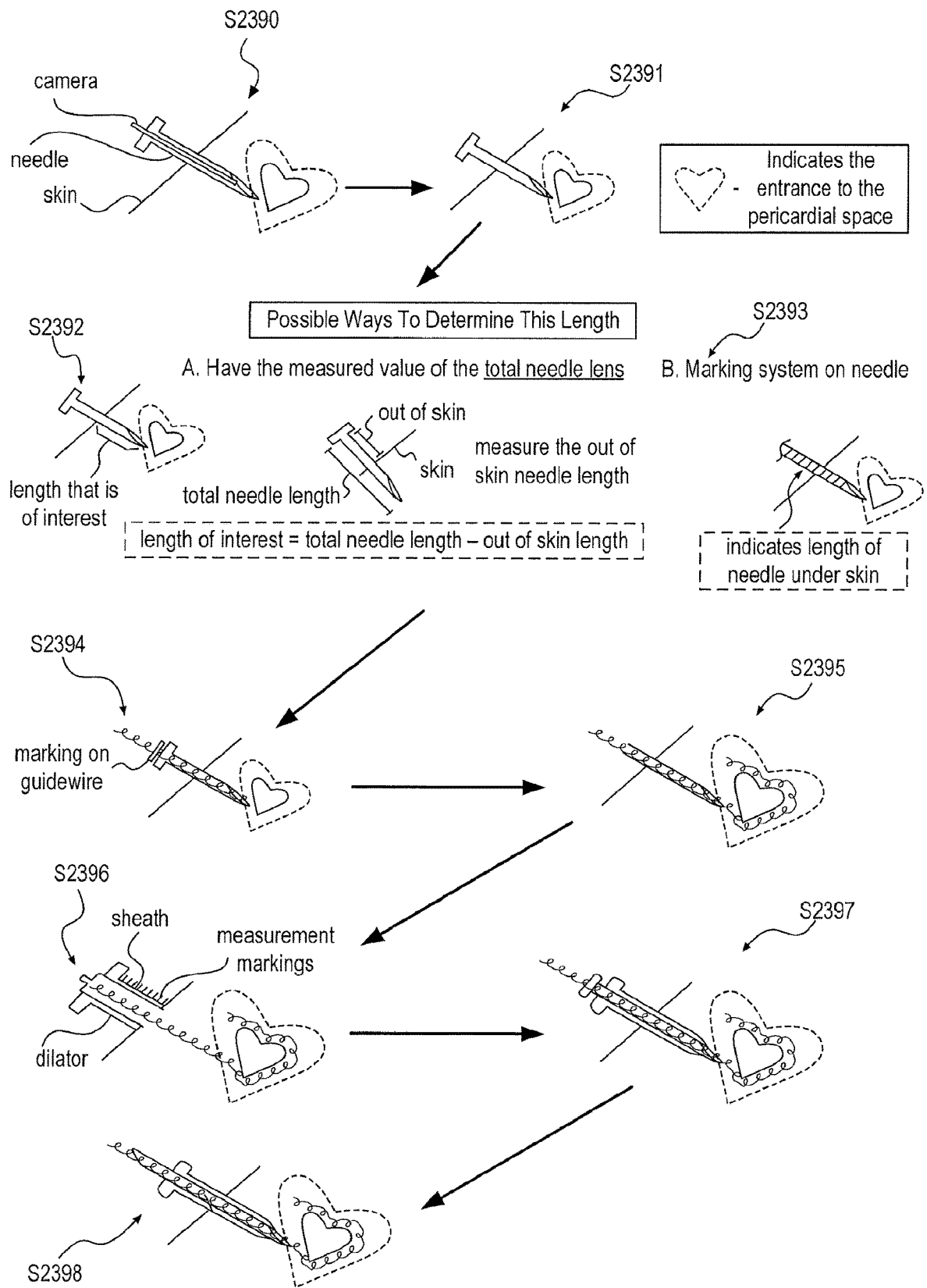
FIG. 23 is an illustration of a flowchart wherein delivery and access tolls may be preloaded onto a needle, according to an exemplary embodiment of the present disclosure.

According to another embodiment, access of the pericardial space may be gained analytically. To this end, markings and measurements may be disposed on a guidewire, a dilator, and a sheath to ensure that procedural tools are in appropriate locations. FIG. 23 is an illustrated flowchart of this approach. First, access to the pericardial space may be gained through a camera down a needle stick S2390.

Once access to the pericardial space has been established, the camera may be removed from the needle while the needle remains in position within the pericardial space S2391. Next, the length of the needle inserted into the skin is calculated by determining a difference between a length of the needle outside the incision site from a known total length of the needle S2392. In another embodiment, the needle may have ruler markings S2393. Once the length of the needle inserted into the skin has been calculated, a guidewire may be inserted into the needle such that the guidewire reaches the tip of the needle at the entrance to the pericardial space S2394. This may be accomplished by defining a pre-marked location on the guidewire indicating the length of the needle. Then, the guidewire may be pushed into the pericardial space S2395. Because the length of the guidewire being inserted into the pericardial space may be of interest, the guidewire length may be noted by additional gradations, markings, or pre-markings provided before the surgery indicating a length of the guidewire that should be inserted into the pericardial space or may be marked on the guidewire during the operation. After the insertion of the guidewire into the pericardial space, the sheath and dilator complex are placed onto the guidewire and pushed to a position such that the tip of the dilator touches the skin 52396. In order to allow the tip of the dilator to be placed at the entrance of the pericardial space, the sheath and dilator may include measurements or markings on a visible side. Therefore, the dilator and sheath may be pushed to the entrance of the pericardial space according to a previously determined length of the needle underneath the skin 52397. A length of the dilator and sheath complex that may be inserted into the pericardial space may be a pre-determined length, such as the length of the needle, in order to ensure insertion of the sheath within the pericardial space 52398. In another embodiment, additional markings may be made on the sheath and dilator complex to ensure a pre-determined length of the sheath and dilator complex be inserted within the pericardial space. Finally, the guidewire and dilator may be removed from the pericardial space, allowing for access to the pericardial space via the sheath.

Figure 24:
FIG. 24 is a flowchart describing accessing a pericardial space analytically, according to an exemplary embodiment of the present disclosure.

FIG. 24 is a flowchart of the above-described approach. First, access to the pericardial space may be gained through a camera down a needle stick. Next the camera may be removed while the needle stick remains such that a length of the needle underneath the skin may be determined. To this end, the length of the needle underneath the skin may be calculated as a difference between the total length of the needle and the length of the needle outside of the skin, wherein the total length of the needle is a known value. Moreover, the needle stick may have measurement markings indicating the length of the needle underneath the skin. Next, a guidewire may be inserted into the needle such that it is positioned at a tip of the needle. In an embodiment, this length may indicated by markings on the guidewire. Subsequently, the guidewire may be pushed into the pericardial space. A sheath and dilator complex may be moved over the guidewire and up to the skin. Then, the sheath and dilator complex may be pushed to the pericardial entrance according to the calculated length of the needle underneath the skin. From this position, the sheath and dilator complex may be inserted into the pericardial space. The guidewire and dilator may then be removed and cardiac therapies may be delivered into the pericardial space via the sheath. Positioning of the cardiac therapy may be visually confirmed via camera within the lumen of the cardiac therapy.

Figure 25:
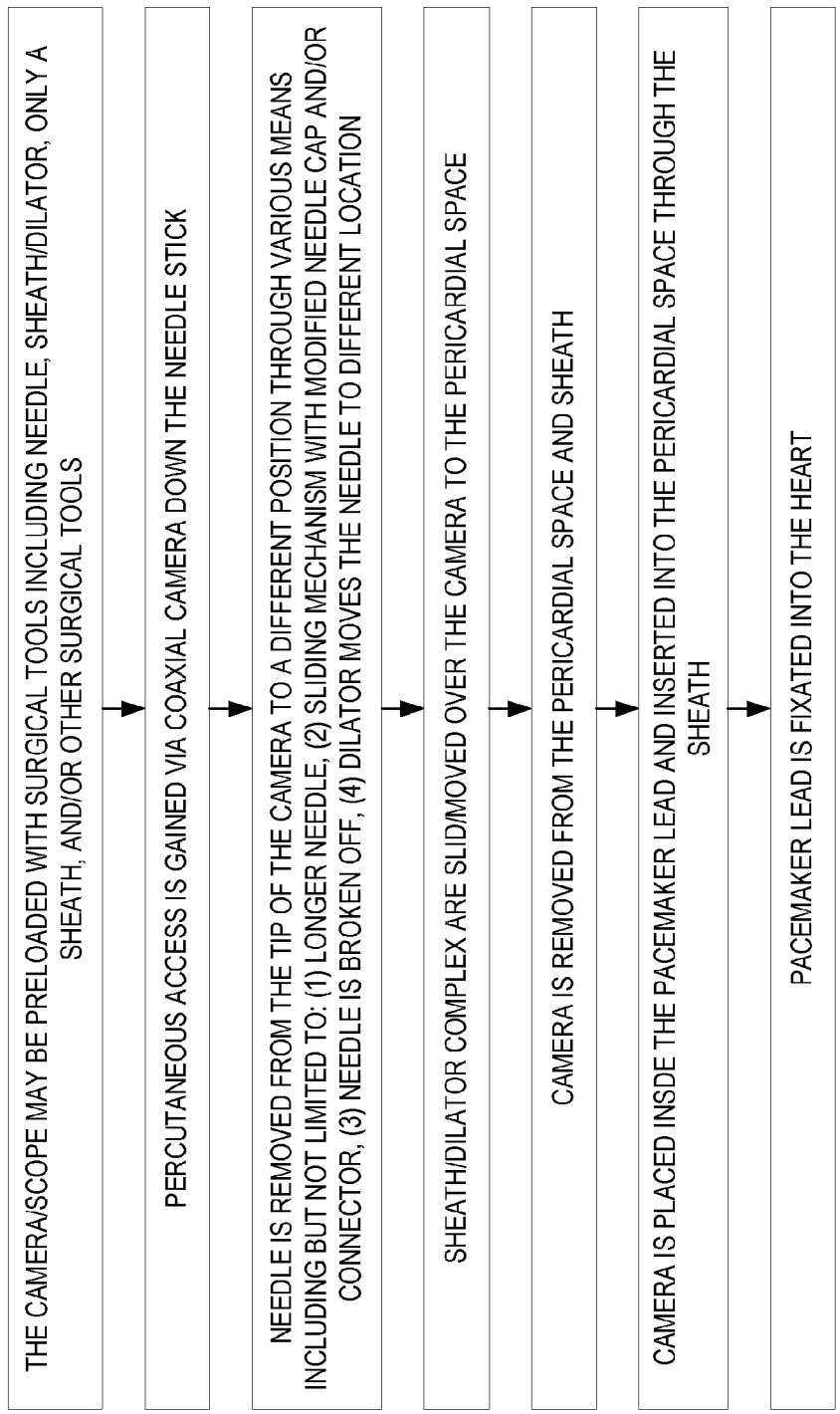
FIG. 25 is a flowchart describing a preloaded needle for pericardial access, according to an exemplary embodiment of the present disclosure.

According to another embodiment, percutaneous access to the pericardial space may be gained via a preloaded access tool, thus eliminating the need for a guidewire. A generalized flowchart of this approach is shown in FIG. 25. Initially, appropriate access tools may be preloaded on a fiber scope, the appropriate access tools including but not limited to a needle, a sheath and dilator complex, a sheath, and other procedural tools for promoting safety and efficacy.

Once preloaded, therapies may be delivered to the pericardial space via the following approach. Initially, pericardial access may be obtained through direct visualization via a camera down a needle stick. The needle may then be removed from the dilator and sheath complex such that the dilator and sheath complex may be used to access the pericardial space. To this end, the needle may be removed in variety of ways.

Figure 26:
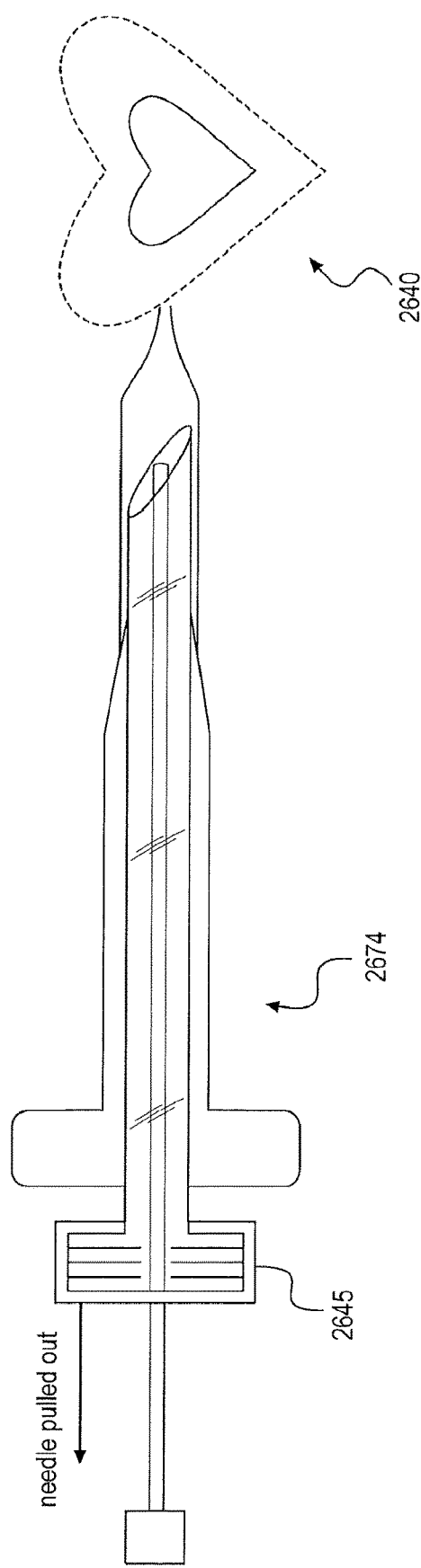
FIG. 26 is a schematic of a needle and a sheath and dilator complex, according to an exemplary embodiment of the present disclosure.
Figure 27:
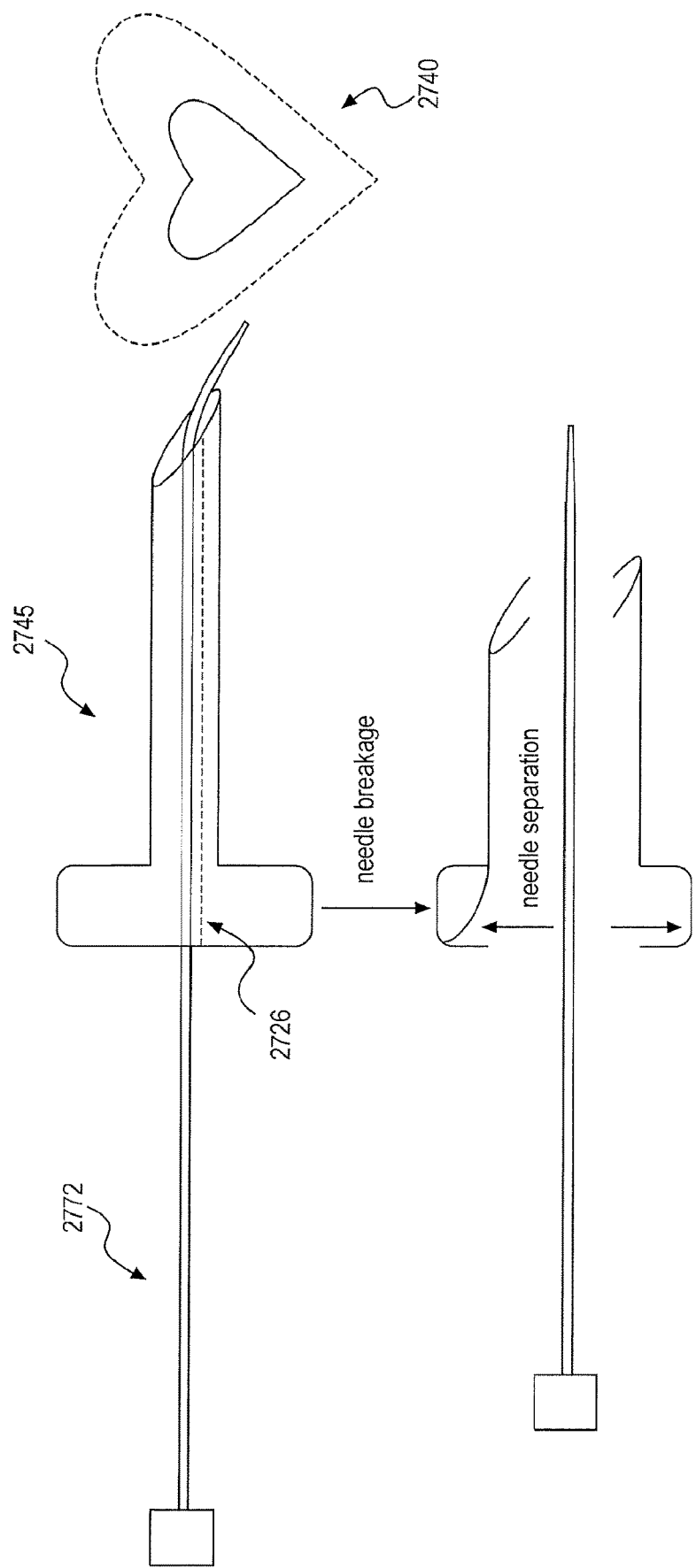
FIG. 27 is a schematic of a separable needle, according to an exemplary embodiment of the present disclosure.
Figure 28:
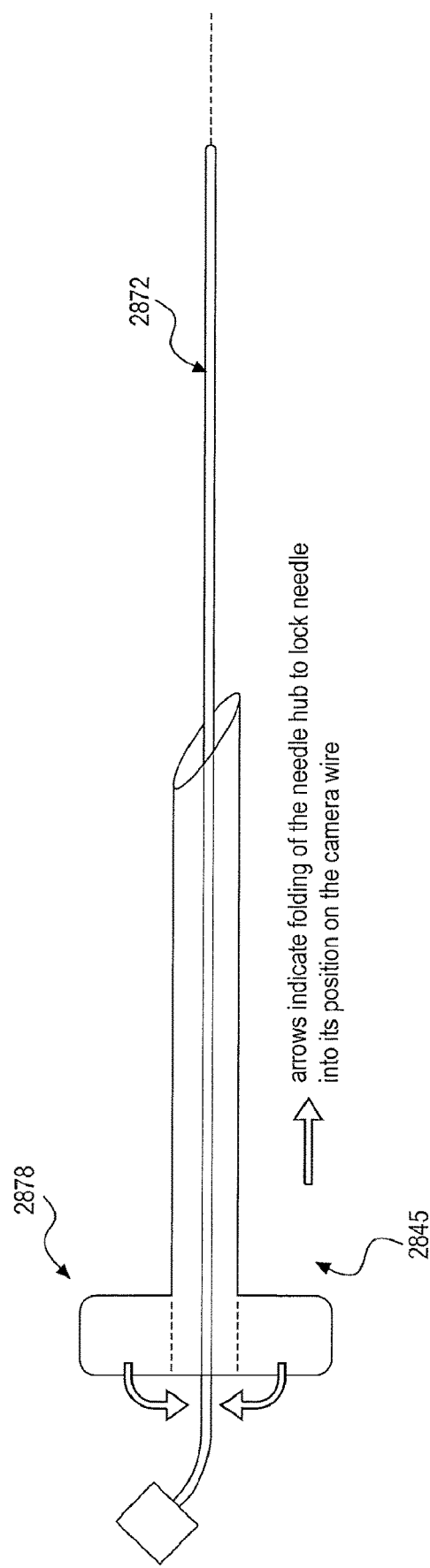
FIG. 28 is a schematic of a locking mechanism for securing a needle to a camera, according to an exemplary embodiment of the present disclosure.
Figure 29:
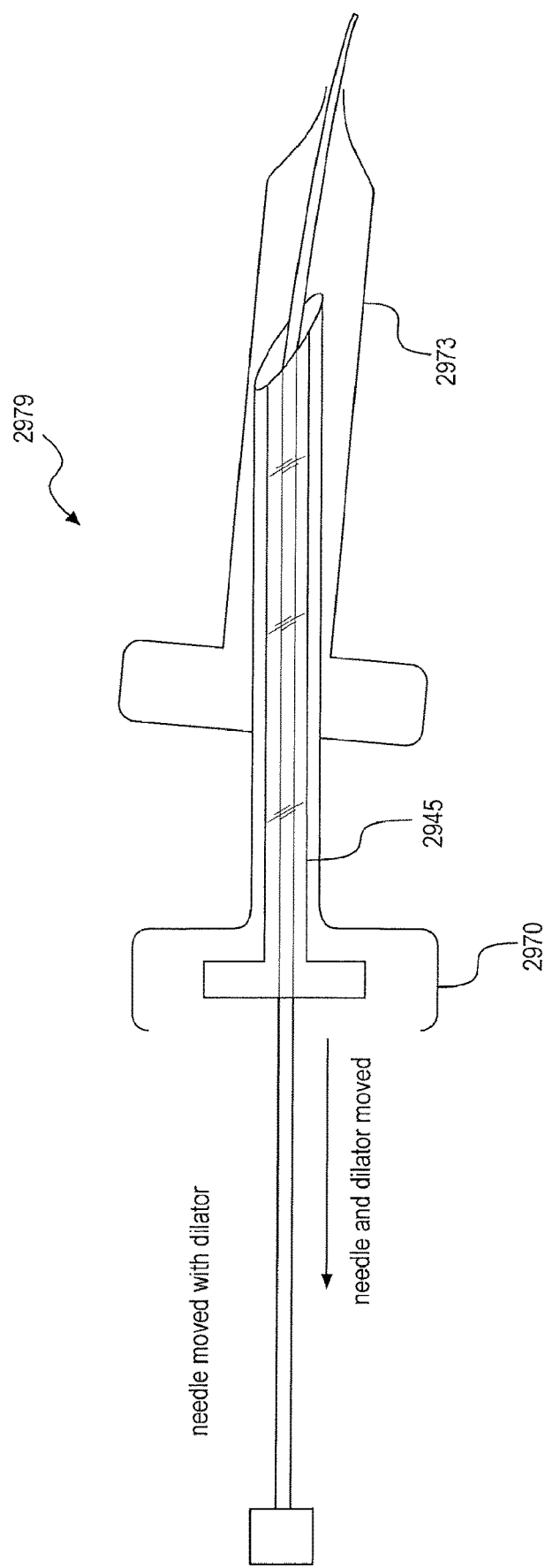
FIG. 29 is a schematic of a needle combined with a dilator, according to an exemplary embodiment of the present disclosure.

In a first embodiment, and as shown in FIG. 26, a needle 2645 longer than a sheath and dilator complex 2674 may be deployed in order to remove the needle 2645 from the back of the sheath and dilator complex 2674 via applied force. In a second embodiment, the dilator and sheath complex 2674 may be fabricated to be shorter than a standard needle length such that the needle 2645 extends beyond the dilator and sheath complex 2674 when it is preloaded. In a third embodiment, a needle 2745 may be split along at least one division line 2726 when force is applied at a hub, allowing the needle 2745 to be removed from cabling of a camera 2772, as shown in FIG. 27. In the third embodiment, following removal of the needle 2845 from a dilator and sheath complex, the needle 2845 may be slid backwards along the camera 2872 and secured by clamping a hub 2878 to the camera 2872, thus preventing the needle 2845 from sliding back within the dilator and sheath complex, as shown in FIG. 28. In a fourth embodiment, a needle 2945 may be embedded within a dilator 2970 with over molding such that pericardial access may be obtained with a needle and dilator assembly, as shown in FIG. 29. The dilator and needle assembly 2979 may then be removed, simultaneously, from a sheath 2973.

Figure 30:
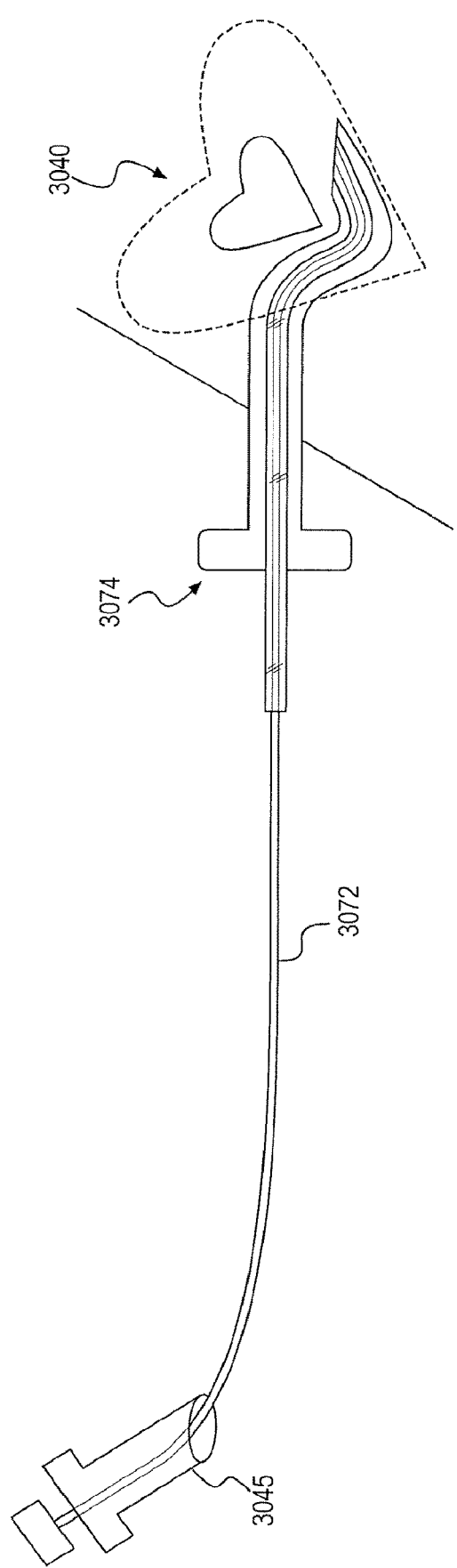
FIG. 30 is a schematic of a sheath and a dilator being advanced into the pericardial space, according to an exemplary embodiment of the present disclosure.
Figure 31:
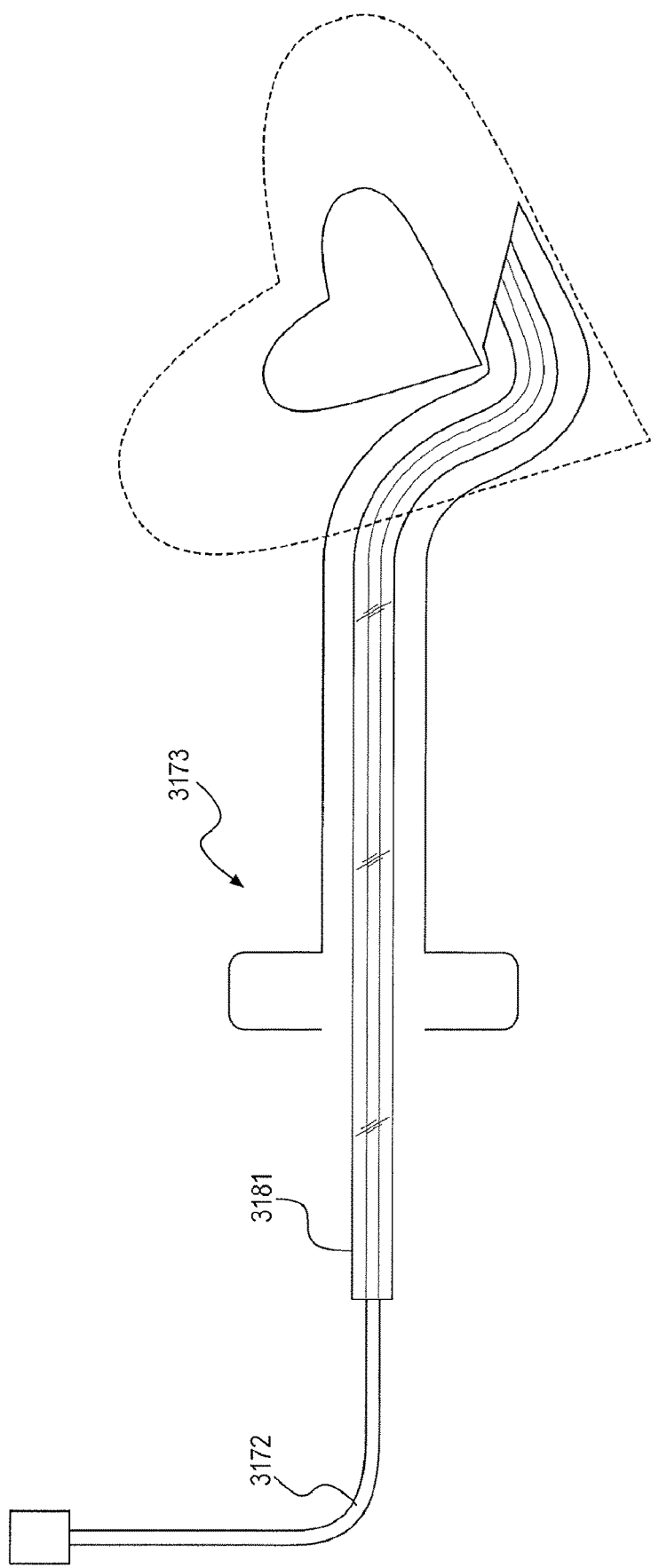
FIG. 31 is a schematic of a camera placed within a pacing lead and advanced through a sheath into a pericardial space, according to an exemplary embodiment of the present disclosure.

Following any of the above described approaches, comprising access of the pericardial space via a needle and removal of the needle from a dilator and sheath complex, the dilator and sheath complex and other procedural tools may be advanced into the pericardial space over a camera. A distance the dilator and sheath complex may move over cabling of the camera may depend on the initial location of the dilator and sheath complex. For example, the dilator and sheath complex may initially be positioned at a distance from the camera tip and need to be slid over the cabling of the camera into the pericardial space. As the dilator and sheath complex 3074 is pushed towards the tip of the camera 3072, the camera 3072 may serve as a guide into the pericardial space of a heart 3040, as shown in FIG. 30. The camera 3072 may then be inserted within the pericardial space for direct visualization, thus assisting in confirmation of the procedural tools, as well as efficacy and safety. Modifications to the dilator and sheath complex 3074 may include changes in thickness, diameter, degree of tapering, and length. Next, when the dilator and sheath complex, and other procedural tools, are within the pericardial space, the camera may be removed via the dilator and sheath complex. A pacemaker lead may then be inserted into the pericardial space through a lumen of the dilator and sheath complex. In an embodiment, insertion of the pacemaker lead may involve direct visualization via insertion of a camera within the lumen of the pacemaker lead, as shown in FIG. 31. Direct visualization in this manner may improve configuration of the location of the sheath 3173 within the pericardial space, resulting in the removal of the camera 3172 from the sheath 3173 and the insertion of the pacemaker lead 3181. In an embodiment, the pacemaker lead 3181 may contain a camera within its lumen providing visualization when entering the pericardial space. In another embodiment, the camera 3172 initially used for visualization may be subsequently placed within the pacemaker lead 3181 for implantation. Additional adapters may be used to either prevent or encourage movement of the camera within the pacemaker lead, including camera rotation. Once the pacemaker lead is within the pericardial space, it may be fixated into the heart.

According to another embodiment, the pacemaker lead may be inserted by placing a camera down the lumen of the pacemaker lead, wherein a needle has been preloaded with the pacemaker lead. After gaining access to the pericardial space through direct visualization via the camera within the needle, the pacemaker lead may be advanced into the pericardial space. The needle may then be broken along two division lines in order to remove it from the pacemaker lead and camera.

FIG. 32 is a flowchart of the above-described embodiments. First, a camera may be preloaded with requisite procedural tools including but not limited to a needle, a sheath and dilator complex, a sheath, and other procedural tools. Next, percutaneous access may be gained via camera positioned down the lumen of a needle stick. The needle may be removed from the tip of the camera and placed in a different position via a variety of means, including but not limited to a longer needle, a sliding mechanism with a modified needle cap or connector, a breakable needle, and a repositioned dilator. In an embodiment, the breakable needle may separable along a perforation line or other biasing feature. The sheath and dilator complex may then be moved over the camera and into the pericardial space. After the camera is removed from the pericardial space and the sheath, the camera may be placed inside the pacemaker lead and inserted into the pericardial space via the sheath. Subsequently, the pacemaker lead may be fixated into the heart.

Embodiments of the present disclosure may also be as set forth in the following parentheticals.

(1) An apparatus for transcutaneous delivery of a medical therapy, comprising a shell, a core, concentrically disposed within the shell, including one or more working channels, the one or more working channels including a first working channel and a second working channel, a proximal flange disposed at a proximal end of the shell, and a distal flange disposed at a distal end of the shell, wherein the first working channel and the second working channel are offset by a triangulation angle, the triangulation angle describing a relative arrangement of a longitudinal axis of the first working channel and a longitudinal axis of the second working channel, and wherein an aperture of the first working channel is larger than an aperture of the second working channel.

(2) The apparatus according to (1), wherein the distal flange is a mutable flange.

(3) The apparatus according to either (1) or (2), wherein the mutable flange is an inflatable flange configured to secure the apparatus against an internal surface of a chest wall, the inflatable flange inflatable via introduction of a fluid.

(4) The apparatus according to any of (1) to (3), wherein the mutable flange is fabricated from a shape-memory material, the shape-memory material configured to return to a pre-deformed state, securing the apparatus against an internal surface of a chest wall.

(5) The apparatus according to any of (1) to (4), wherein the mutable flange is comprised of one or more struts having one or more biasing features, the one or more struts being deformable at each of the one or more biasing features.

(6) The apparatus according to any of (1) to (5), wherein the triangulation angle is adjustable.

(7) The apparatus according to any of (1) to (6), wherein the triangulation angle is 25°.

(8) The apparatus according to any of (1) to (7), wherein the core is separable from the shell, the separation of the core from the shell creating a modular working channel within the shell.

(9) The apparatus according to any of (1) to (8), wherein the apparatus is separable along a division line, the division line being configured to divide the apparatus into a plurality of components.

(10) The apparatus according to any of (1) to (9), further comprising one or more plugs coupled to the core via one or more tethers, the one or more plugs configured to modify an aperture of a corresponding one of the one or more working channels.

(11) A method of manufacturing an apparatus for transcutaneous delivery of a medical therapy, comprising forming, via a subtractive manufacturing modality, a shell having a proximal flange disposed at a proximal end of the shell and a distal flange disposed at a distal end of the shell, forming, via the subtractive manufacturing modality, a core including one or more working channels, the one or more working channels including a first working channel and a second working channel, and positioning the core concentrically within the shell, wherein the first working channel and the second working channel are offset by a triangulation angle, the triangulation angle describing a relative arrangement of a longitudinal axis of the first working channel and a longitudinal axes of the second working channel, and wherein an aperture of the first working channel is larger than an aperture of the second working channel.

(12) The method of manufacture according to (11), wherein the distal flange is a mutable flange.

(13) The method of manufacture according to either (11) or (12), wherein the mutable flange is an inflatable flange configured to secure the apparatus against an internal surface of a chest wall, the inflatable flange inflatable via introduction of a fluid.

(14) The method of manufacture according to any of (11) to (13), wherein the mutable flange is fabricated from a shape-memory material, the shape-memory material configured to return to a pre-deformed state, securing the apparatus against an internal surface of a chest wall.

(15) The method of manufacture according to any of (11) to (14), wherein the mutable flange is comprised of one or more struts having one or more biasing features, the one or more struts being deformable at each of the one or more biasing features.

(16) The method of manufacture according to any of (11) to (15), wherein the triangulation angle is 25°.

(17) The method of manufacture according to any of (11) to (16), wherein the core is separable from the shell, the separation of the core from the shell creating a modular working channel within the shell.

(18) The method of manufacture according to any of (11) to (17), wherein the apparatus is separable along a division line, the division line being configured to divide the apparatus into a plurality of components.

(19) The method of manufacture according to any of (11) to (18), wherein the subtractive manufacturing modality is machining.

(20) A method of manufacturing an apparatus for transcutaneous delivery of a medical therapy, comprising forming, via an additive manufacturing modality, a shell having a proximal flange disposed at a proximal end of the shell and a distal flange disposed at a distal end of the shell, and forming, via the additive manufacturing modality, a core disposed concentrically within the shell and including one or more working channels, the one or more working channels including a first working channel and a second working channel, wherein the first working channel and the second working channel are offset by a triangulation angle, the triangulation angle describing a relative arrangement of a longitudinal axis of the first working channel and a longitudinal axes of the second working channel, and wherein an aperture of the first working channel is larger than an aperture of the second working channel.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus for transcutaneous delivery of a medical therapy, comprising:
   a shell;
   a core, concentrically disposed within the shell, including one or more working channels, the one or more working channels including a first working channel and a second working channel;
   a proximal flange disposed at a proximal end of the shell; and
   a distal flange disposed at a distal end of the shell,
   wherein the first working channel and the second working channel are offset by a triangulation angle, the triangulation angle describing a relative arrangement of a longitudinal axis of the first working channel and a longitudinal axis of the second working channel, and wherein an aperture of the first working channel is larger than an aperture of the second working channel, and wherein the distal flange is foldable and held in position by a spacer that maintains a distance between the proximal flange and a surface of the core.

2. The apparatus according to claim 1, wherein the distal flange is a mutable flange.

3. The apparatus according to claim 2, wherein the mutable flange is an inflatable flange configured to secure the apparatus against an internal surface of a chest wall, the inflatable flange inflatable via introduction of a fluid.

4. The apparatus according to claim 2, wherein the mutable flange is fabricated from a shape-memory material, the shape-memory material configured to return to a pre-deformed state, securing the apparatus against an internal surface of a chest wall.

5. The apparatus according to claim 2, wherein the mutable flange is comprised of one or more struts having one or more biasing features, the one or more struts being deformable at each of the one or more biasing features.

6. The apparatus according to claim 1, wherein the triangulation angle is adjustable.

7. The apparatus according to claim 1, wherein the triangulation angle is 25°.

8. The apparatus according to claim 1, wherein the core is separable from the shell, the separation of the core from the shell creating a modular working channel within the shell.

9. The apparatus according to claim 1, wherein the apparatus is separable along a division line, the division line being configured to divide the apparatus into a plurality of components.

10. The apparatus according to claim 1, further comprising one or more plugs coupled to the core via one or more tethers, the one or more plugs configured to modify an aperture of a corresponding one of the one or more working channels.

11. A method of manufacturing an apparatus for transcutaneous delivery of a medical therapy, comprising:
    forming, via a subtractive manufacturing modality, a shell having a proximal flange disposed at a proximal end of the shell and a distal flange disposed at a distal end of the shell;
    forming, via the subtractive manufacturing modality, a core including one or more working channels, the one or more working channels including a first working channel and a second working channel; and
    positioning the core concentrically within the shell,
    wherein the first working channel and the second working channel are offset by a triangulation angle, the triangulation angle describing a relative arrangement of a longitudinal axis of the first working channel and a longitudinal axis of the second working channel, and
    wherein an aperture of the first working channel is larger than an aperture of the second working channel, and
    wherein the distal flange is foldable and held in position by a spacer that maintains a distance between the proximal flange and a surface of the core.

12. The method of manufacture according to claim 11, wherein the distal flange is a mutable flange.

13. The method of manufacture according to claim 12, wherein the mutable flange is an inflatable flange configured to secure the apparatus against an internal surface of a chest wall, the inflatable flange inflatable via introduction of a fluid.

14. The method of manufacture according to claim 12, wherein the mutable flange is fabricated from a shape-memory material, the shape-memory material configured to return to a pre-deformed state, securing the apparatus against an internal surface of a chest wall.

15. The method of manufacture according to claim 12, wherein the mutable flange is comprised of one or more struts having one or more biasing features, the one or more struts being deformable at each of the one or more biasing features.

16. The method of manufacture according to claim 11, wherein the triangulation angle is 25°.

17. The method of manufacture according to claim 11, wherein the core is separable from the shell, the separation of the core from the shell creating a modular working channel within the shell.

18. The method of manufacture according to claim 11, wherein the subtractive manufacturing modality is machining.

19. A method of manufacturing an apparatus for transcutaneous delivery of a medical therapy, comprising:
    forming, via an additive manufacturing modality, a shell having a proximal flange disposed at a proximal end of the shell and a distal flange disposed at a distal end of the shell; and
    forming, via the additive manufacturing modality, a core disposed concentrically within the shell and including one or more working channels, the one or more working channels including a first working channel and a second working channel,
    wherein the first working channel and the second working channel are offset by a triangulation angle, the triangulation angle describing a relative arrangement of a longitudinal axis of the first working channel and a longitudinal axis of the second working channel, and
    wherein an aperture of the first working channel is larger than an aperture of the second working channel, and
    wherein the distal flange is foldable and held in position by a spacer that maintains a distance between the proximal flange and a surface of the core.

20. The method of manufacture according to claim 19, wherein the additive manufacturing modality is stereolithorgraphy.

* * * * *